(12) United States Patent
Robert et al.

(10) Patent No.: US 10,960,388 B2
(45) Date of Patent: Mar. 30, 2021

(54) PHOTOCHEMICAL COMPOSITION AND USE THEREOF FOR PRODUCING $CH_4$ FROM $CO_2$ AND/OR CO

(71) Applicants: UNIVERSITE PARIS DIDEROT PARIS 7, Paris (FR); CENTRE NATIONAL DE LA RECHERCHE SCIENTIFIQUE (CNRS), Paris (FR)

(72) Inventors: Marc Robert, Paris (FR); Julien Bonin, Massy (FR)

(73) Assignees: UNIVERSITE PARIS DIDEROT PARIS 7, Paris (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 282 days.

(21) Appl. No.: 15/879,650

(22) Filed: Jan. 25, 2018

(65) Prior Publication Data
US 2019/0224659 A1    Jul. 25, 2019

(51) Int. Cl.
*B01J 31/18* (2006.01)
*B01J 37/34* (2006.01)
(Continued)

(52) U.S. Cl.
CPC ............. *B01J 31/183* (2013.01); *B01J 37/34* (2013.01); *C07C 1/10* (2013.01); *C07C 1/12* (2013.01); *C07D 487/22* (2013.01); *B01J 35/004* (2013.01); *B01J 2231/648* (2013.01); *C07C 2531/18* (2013.01); *C07C 2531/22* (2013.01); *G01N 30/7206* (2013.01); *G01N 2030/025* (2013.01)

(58) Field of Classification Search
None
See application file for complete search history.

(56) References Cited

U.S. PATENT DOCUMENTS

2015/0096899 A1    4/2015   Costentin et al.

FOREIGN PATENT DOCUMENTS

WO   WO 2015/169763 A1   11/2015
WO   WO 2016/124611 A1    8/2016

OTHER PUBLICATIONS

Rao et al. ChemSusChem 2017, 10, 4447-4450 (Year: 2017).*
(Continued)

*Primary Examiner* — Yun Qian
(74) *Attorney, Agent, or Firm* — Birch, Stewart, Kolasch & Birch, LLP

(57) ABSTRACT

The present invention relates to photochemical compositions comprising:
- a solution comprising an organic solvent, preferably selected from dimethylformamide, acetonitrile, and mixtures thereof with water,
- a sacrificial electron donor;
- a proton donor having a pKa in acetonitrile greater than or equal to 28;
- a photosensitizer whose reduced state has a standard redox potential more negative than −1.45 V vs SCE; and
- a metal porphyrin complex of formula (I) as defined in claim 1, useful in the production of $CH_4$ from $CO_2$ or CO by photochemical catalysis, to a photochemical cell comprising same and to a method for producing $CH_4$ from $CO_2$ or CO by photochemical catalysis using same.

18 Claims, 6 Drawing Sheets

(51) Int. Cl.
  *C07C 1/10* (2006.01)
  *C07C 1/12* (2006.01)
  *C07D 487/22* (2006.01)
  *G01N 30/02* (2006.01)
  *G01N 30/72* (2006.01)
  *B01J 35/00* (2006.01)

(56) References Cited

OTHER PUBLICATIONS

Rao et al. ChemSusChem Supporting Information (Year: 2017).*
Yasu et al. Angew. Chem. Int. Ed, 2012, 51, 9567-9571 (Year: 2012).*
Zhang et al. (J. Phys. Chem. C, 119, 4645-4654 (Year: 2015).*
Robert et al. (Nature, 548, 74-78 (Year: 2017).*
Alsabeh et al., "Iron-catalyzed Photoreduction of Carbon Dioxide to Synthesis Gas," Catal. Sci. Technol., vol. 6, 2016 (Published Dec. 16, 2015), pp. 3623-3630.
Azcarate et al., "Through-Space Charge Interaction Substituent Effects in Molecular Catalysis Leading to the Design of the Most Efficient Catalyst of $CO_2$-to-CO Electrochemical Conversion," J. Am. Chem. Soc., vol. 138, 2016 (Published Nov. 11, 2016), pp. 16639-16644.
Bonin et al., "Homogeneous Photocatalytic Reduction of $CO_2$ to CO Using Iron(0) Porphyrin Catalysts: Mechanism and Intrinsic Limitations," ChemCatChem, vol. 6, 2014 (Published online Sep. 12, 2014), pp. 3200-3207.
Bonin et al., "Selective and Efficient Photocatalytic $CO_2$ Reduction to CO Using Visible Light and an Iron-Based Homogeneous Catalyst," J. Am. Chem. Soc., vol. 136, 2014 (Published Nov. 14, 2014), pp. 16768-16771.
Costentin et al., "A Local Proton Source Enhances $CO_2$ Electroreduction to CO by a Molecular Fe Catalyst," Science, vol. 338, No. 90, Oct. 5, 2012, pp. 90-94 (6 pages total).
Costentin et al., "Current Issues in Molecular Catalysis Illustrated by Iron Porphyrins as Catalysts of the $CO_2$-to-CO Electrochemical Conversion," Acc. Chem. Res., vol. 48, 2015 (Published Nov. 12, 2015), pp. 2996-3006.
Costentin et al., "Efficient and Selective Molecular Catalyst for the $CO_2$-to-CO Electrochemical Conversion in Water," PNAS, vol. 112, No. 22, Jun. 2, 2015, pp. 6882-6886.
Dedeian et al., "A New Synthetic Route to the Preparation of a Series of Strong Photoreducing Agents: fac Tris-Ortho-Metalated Complexes of Iridium(III) with Substituted 2-Phenylpyridines," Inorg. Chem., vol. 30, No. 8, 1991, pp. 1685-1687.
Piao et al., "Efficiently Converting $CO_2$ into $C_2H_4$ Using a Porphyrin-Graphene Composite Photocatalyst," Aust. J. Chem., vol. 69, 2016 (Published online Jun. 26, 2015), pp. 27-32.
Rao et al., "Non-sensitized Selective Photochemical Reduction of $CO_2$ to CO under Visible Light with an Iron Molecular Catalyst," Chem. Commun, vol. 53, 2017 (Published Feb. 13, 2017), pp. 2830-2833.
Rao et al., "Visible-light Homogeneous Photocatalytic Conversion of $CO_2$ into CO in Aqueous Solutions with an Iron Catalyst," ChemSusChem, vol. 10, 2017, pp. 4447-4450.
Rao et al., "Visible-light-driven Methane Formation from $CO_2$ with a Molecular Iron Catalyst," Nature, vol. 548, Aug. 3, 2017, pp. 74-77 (8 pages total).
Wu et al., "A Carbon-based Photocatalyst Efficiently Converts $CO_2$ to $CH_4$ and $C_2H_2$ Under Visible Light," Green Chemistry, vol. 16, 2014 (Published Jan. 8, 2014), pp. 2142-2146.

* cited by examiner

PHOTOCHEMICAL COMPOSITION AND USE THEREOF FOR PRODUCING CH$_4$ FROM CO$_2$ AND/OR CO

TECHNICAL FIELD

The present invention relates to photochemical compositions, useful in the production of CH$_4$ from CO$_2$ or CO by photochemical catalysis, and to a method for producing CH$_4$ from CO$_2$ or CO by photochemical reduction using said photochemical compositions.

BACKGROUND OF THE INVENTION

Converting CO$_2$ into fuel or chemical feedstock compounds could in principle reduce fossil fuel consumption and climate-changing CO$_2$ emissions. One strategy aims for electrochemical conversions powered by electricity from renewable sources, but photochemical approaches driven by sunlight are also conceivable. A considerable challenge in both approaches is the development of efficient and selective catalysts, ideally based on cheap and earth-abundant elements rather than expensive precious metals. Of the molecular photo- and electrocatalysts reported to date, only a few systems are stable and selective for CO$_2$ reduction; moreover, these systems primarily produce CO or HCOOH, while examples of catalysts capable of generating even low to moderate yields of highly reduced hydrocarbons remain rare.

Iron tetraphenylporphyrins electrochemically reduced to the Fe$^0$ species have been shown to be the most efficient molecular catalysts for the CO$_2$-to-CO conversion. The nucleophilic Fe center binds to CO$_2$ and the Fe—CO$_2$ adduct is further protonated and reduced to afford CO upon cleavage of one C—O bond (see for instance Azcarate et al., *J. Am. Chem. Soc.* 138, 16639-16644 (2016) and Costentin et al., *Acc. Chem. Res.* 48, 2996-3006 (2015), as well as US 2015/0096899, WO 2015/169763 and WO 2016/124611).

Tetraphenylporphyrin-based systems were described for the production of ethylene (C$_2$H$_4$) or acetylene (C$_2$H$_2$) and methane under visible light irradiation, using graphene as charge transfer mediator and a copper or cobalt tetra(hydroxyphenyl)porphyrin (CuTHPP and CoTHPP) as light exciter (see respectively Piao et al. *Aust. J. Chem.* 2016, 69, 27-32 and Wu et al. *Green Chemistry* 2014, 16, 2142-2146). These systems do not comprise any photosensitizers or proton donors other than H$_2$O.

Fe-p-TMA was used as a photocatalyst without a photosensitizer under visible light irradiation with triethylamine as sacrificial electron donor, which led to the selective formation of CO, and no side products except for limited quantities of H$_2$ were observed (see Rao et al., *Chem. Commun.* 2017, 53, 2830-2833). The same results were obtained in systems devoid of any photosensitizer using iron tetra(dihydroxyphenyl)porphyrin and fluorinated analogues (Bonin et al., *ChemCatChem* 2014, 6, 3200-3207).

Other systems using iron tetra(dihydroxyphenyl)porphyrin as photocatalyst and 9-cyanoanthracene as photosensitizer produced CO from CO$_2$, but failed at producing methane (Bonin et al., *J. Am. Chem. Soc.* 2014, 136, 16768-16771), as well as a system comprising Fe-p-TMA and purpurin as photosensitizer (Rao et al., *ChemSusChem* 2017, 10, 4447-4450).

There is thus still a need for an efficient and selective photochemical systems based on cheap and earth-abundant elements able to produce hydrocarbons such as methane from CO$_2$ and/or CO under visible light irradiation, preferably as homogeneous photochemical systems.

SUMMARY OF THE INVENTION

Surprisingly, the Inventors showed that an iron tetraphenylporphyrin can catalyze the eight-electron reduction of CO$_2$ to methane upon visible light irradiation in the presence of a photosensitizer having a standard redox potential more negative than −1.45 V vs SCE in the reduced state. The system, operated in the presence of a photosensitizer and a sacrificial electron donor, operates stably over several days. While CO is the main product of the direct CO$_2$ photochemical reduction reaction, methane is obtained in good yields and with good selectivity. In particular, a two-pot procedure to first reduce CO$_2$ to CO and subsequently CO generates methane with a selectivity of up to 82% and a quantum yield of up to 0.22% (see Rao et al., *Nature* 2017, 548, 74-77).

Of note, purpurin does not qualify as (organic) photosensitizer having a standard redox potential more negative than −1.45 V vs SCE in the reduced state. This may be the reason why Rao et al. (*ChemSusChem* 2017, 10, 4447-4450) did not observe methane formation in their experiments.

Therefore, in a first aspect, the present invention relates to a photochemical composition comprising:
- a solution comprising an organic solvent, preferably selected from dimethylformamide and acetonitrile, or mixture thereof with water;
- a sacrificial electron donor;
- a photosensitizer whose reduced state has a standard redox potential more negative than −1.45 V vs SCE; and
- a metal porphyrin complex of formula (I):

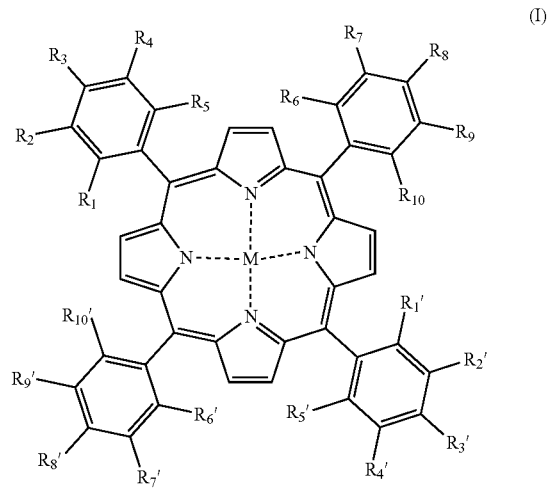

wherein:
M represents a transition metal ion, preferably selected from iron, cobalt and copper,
R$_1$ to R$_{10}$ and R$_1'$ to R$_{10}'$ are independently selected from the group consisting of H, OH, F, C$_1$-C$_6$ alcohol, and N$^+$(C$_1$-C$_4$ alkyl)$_3$,
and wherein:
at least one of R$_1$ to R$_5$ is OH and at least one of R$_1'$ to R$_5'$ is OH, or at least one of R$_1$ to R$_5$ is N$^+$(C$_1$-C$_4$ alkyl)$_3$, and at least one of R$_1'$ to R$_5'$ is N$^+$(C$_1$-C$_4$ alkyl)$_3$, and salts thereof.

In another aspect, the invention relates to a photochemical cell comprising the photochemical composition of the invention.

In another aspect, the invention relates to a method for producing methane ($CH_4$) from $CO_2$ or CO, said method comprising:
 a) contacting gaseous $CO_2$ or CO, with a photochemical composition of the invention, to obtain a solution comprising dissolved $CO_2$ and/or CO;
 b) irradiation of said solution with visible light; and
 c) collecting methane.

Without wishing to be bound by theory, the reaction involved in the present invention cannot be qualified as "photocatalysis". Rather, light acts as a source of energy, while the actual catalysis appears as thermal catalysis. Also noteworthy is the fact that the electron source in the method of the invention is the sacrificial electron donor, unlike in electrochemical reactions where the electron source is the electric generator.

DETAILED DESCRIPTION

1. Photochemical Composition

1.1. Solution

As used herein, an "organic solvent" is understood as a solvent consisting of a molecule containing at least one carbon atom, and preferably a C—H bond. An organic solvent is typically liquid at room temperature (between 15° C. and 25° C.) and under atmospheric pressure. Preferred are polar solvents as commonly understood in the art, in particular solvents with a dielectric constant (or more accurately, relative static permittivity) greater than 15. Examples of polar solvents are in particular dimethylformamide and acetonitrile.

In a particular embodiment, the organic solvent is "aqueous", which is understood herein as a mixture of said organic solvent with water, the volume ratio water/organic solvent being for instance comprised between 0.5/99.5 and 95/5, such as between 0.5/99.5 and 70/30. "Aqueous organic solvents" in particular include non-anhydrous solvents. Conversely, an "anhydrous solvent" is devoid of water, or contains only traces of water.

The organic solvent of the solution is advantageously polar, such as dimethylformamide and/or acetonitrile, and may be aqueous.

In a particular embodiment, the solution is devoid of salts. In another particular embodiment, the solution is devoid of buffering agents.

In a particular embodiment, the solution consists of an aqueous organic solvent, preferably a polar aqueous organic solvent such as aqueous acetonitrile, aqueous dimethylformamide or mixtures thereof.

1.2. Photosensitizer

The photosensitizer should be able to efficiently absorb visible light, and efficiently transfer its electrons with the metal porphyrin complex of formula (I) as described above or below.

The photosensitizer may be homogeneous or heterogeneous.

In a particular embodiment, the photosensitizer is homogeneous. In this embodiment, the photosensitizer may be organic or a metal complex.

In case of a homogeneous metal complex photosensitizer, the photosensitizer is preferably a complex of a transition metal, such as an iridium complex. Advantageously, the complex of a transition metal comprises at least two 2-phenylpyridine (ppy) ligand. More advantageously, the complex comprises 3 ppy ligands.

In particular, the photosensitizer may be a metal complex of formula (III):

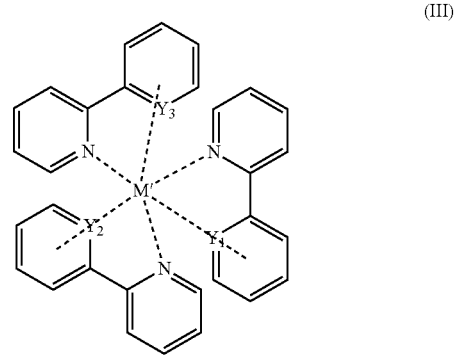

(III)

wherein $Y_1$, $Y_2$ and $Y_3$ are identical or different and are independently selected from $CH_2$ and N, preferably with at least two of $Y_1$, $Y_2$ and $Y_3$ representing N, and M' represents a transition metal such as Co, Cu, Fe, Ni, Rh, Pd, Ag, Au, Ir, Pt, Mo, Cr or Mn, provided that said photosensitizer of formula (III) has a standard redox potential more negative than −1.58 V vs SCE in the reduced state. Advantageously, $Y_1$, $Y_2$ and $Y_3$ are all $CH_2$. Preferably, M' is Ir.

When M' is Ir, the photosensitizer is advantageously $Ir(ppy)_2(bpy)$ or $Ir(ppy)_3$. Preferably, it is $Ir(ppy)_3$.

In another embodiment, the photosensitizer is homogeneous and organic. In this case, the photosensitizer may be an organic compound of formula (II):

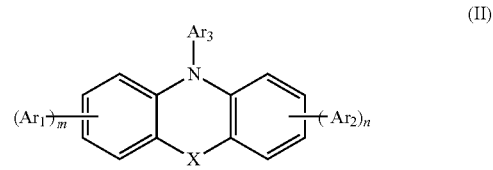

(II)

wherein
X is O or NR, with R representing a $(C_1-C_4)$alkyl or a $(C_1-C_4)$alcohol,
$Ar_1$, $Ar_2$ and $Ar_3$ are independently selected from a biaryl group and a monocyclic or bicyclic 5- to 10-membered aromatic or heteroaromatic ring, optionally substituted by a halogen, CN, OH, m and n are identical or different and are independently 0, 1, 2 or 3.

Preferably X is O. Advantageously, m and n are both 1.

Advantageously, m and n are both 1 and at least one (preferably at least 2 and even more preferably all three) of $Ar_1$, $Ar_2$ and $Ar_3$ represents a bicyclic 5- to 10-membered aromatic ring, optionally substituted by a halogen, CN, OH, or a biaryl group advantageously of formula Ar—Ar'— wherein Ar and Ar' each independently represent a 5- or 6-membered monocyclic aromatic or heteroaromatic group.

In an advantageous embodiment, m and n are both 1 and at least one (preferably at least 2 and even more preferably all three) of $Ar_1$, $Ar_2$ and $Ar_3$ represents a bicyclic 5- to 10-membered aromatic ring, or a biaryl group advantageously of formula Ar—Ar'— wherein Ar and Ar' each independently represent a phenyl or pyridine group.

For instance, the homogeneous organic photosensitizer is:

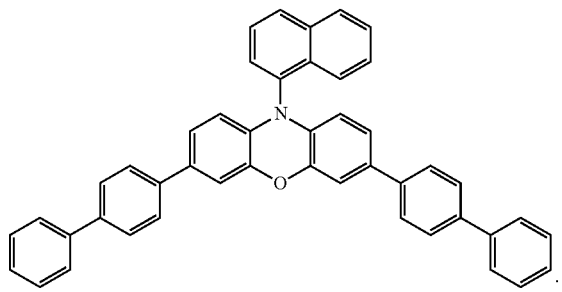 [SMILES: c1ccc(-c2ccc(-c3ccc4c(c3)Oc3cc(-c5ccc(-c6ccccc6)cc5)ccc3N4c3cccc4ccccc34)cc2)cc1]

Advantageously, the concentration of the photosensitizer in the photochemical composition is between 50 μM and 1 mM. The person of skill in the art will determine the appropriate photosensitizer concentration especially upon considering its molar extinction coefficient In another particular embodiment, the photosensitizer is heterogeneous.

1.3. Sacrificial Electron Donor

In a particular embodiment, the sacrificial electron donor is a tertiary amine, advantageously of formula $NR_1R_2R_3$, in which $R_1$, $R_2$ and $R_3$ are identical or different and each independently selected from a $C_1$-$C_6$ alkyl group optionally substituted with OH, $OC_1$-$C_6$ alkyl, or COOH. Advantageously, the tertiary amine is triethylamine, triethanolamine, diisopropylethylamine, ethylenediamine tetraacetic acid, preferably triethylamine.

Alternatively, the sacrificial electron donor may be of formula (IV):

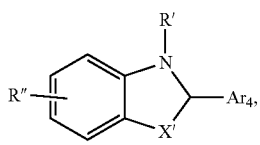

(IV)

wherein

X' is O or NR, with R representing a $(C_1$-$C_4)$alkyl or a $(C_1$-$C_4)$alcohol R' is a $(C_1$-$C_4)$alkyl, R" is a hydrogen, halogen, CN, or a $(C_1$-$C_4)$alkyl, and $Ar_4$ is selected from a monocyclic or bicyclic 5- to 10-membered aromatic or heteroaromatic ring, optionally substituted by a halogen, CN, OH, a biaryl group or a monocyclic 5- or 6-membered aromatic or heteroaromatic ring, said monocyclic 5- or 6-membered aromatic or heteroaromatic ring being optionally substituted by a halogen, CN, OH.

Preferably, in formula (IV), X' is NR with R being a $(C_1$-$C_4)$alkyl, R' is a $(C_1$-$C_4)$alkyl, R" is H, and $Ar_4$ is a biaryl group or a monocyclic 5- or 6-membered aromatic or heteroaromatic ring, optionally substituted by a halogen, CN, OH.

For instance, the tertiary amine is

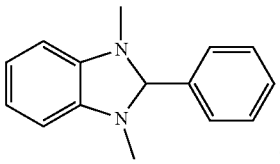

(also called 1,3-Dimethyl-2-phenylbenzimidazoline)

Preferably, the concentration of a sacrificial electron donor in the photochemical composition is between 10 mM and 500 mM.

1.4. Proton Donor

The photochemical composition comprises a proton donor having a pKa in acetonitrile above 28, such as phenol or trifluoroethanol or water. Preferably, the proton donor has a pKa in acetonitrile which is strictly greater than 28, advantageously it is phenol or trifluoroethanol, most preferably it is trifluoroethanol.

In a particular embodiment, the proton donor is the same molecule as the sacrificial electron donor, or a protonated sacrificial electron donor. For instance, when the sacrificial electron donor is triethylamine, the proton donor may be protonated triethylamine $HN^+Et_3$.

In another embodiment, the proton donor is distinct from the sacrificial electron donor. In particular, in this embodiment, the proton donor is not a protonated form of the sacrificial electron donor.

Advantageously, the concentration of a proton donor in the photochemical composition is between 1 mM and 1 M. The person of skill in the art will determine the appropriate proton donor concentration especially upon considering its pKa.

1.5. Metal Porphyrin Complex

According to the present invention, a "homogeneous catalyst" is a catalyst which is contained in the same phase as the reactants. In contrast, a "heterogeneous catalyst" is contained in a phase which differs from the phase of the reactants (here dissolved $CO_2$ and/or CO). Therefore, in the present invention, a "homogeneous catalyst" is soluble in the solution. In particular, the homogeneous catalysts of the invention are soluble in acetonitrile, dimethylformamide and mixture thereof, as well as in aqueous acetonitrile, aqueous dimethylformamide and mixture thereof.

The metal porphyrin complex of the invention is preferably used as a homogeneous catalyst.

M represents a transition metal ion, preferably selected from iron, cobalt and copper. Most preferably, M is iron (Fe).

Preferably, the metal porphyrin complex of formula (I) comprises at least two $N^+(C_1$-$C_4$ alkyl$)_3$ groups.

In particular, at least one of $R_1$ to $R_5$ is $N^+(C_1$-$C_4$ alkyl$)_3$, and at least one of $R_{1'}$ to $R_{5'}$ is $N^+(C_1$-$C_4$ alkyl$)_3$.

In a particular embodiment, the metal porphyrin complex of formula (I) is further characterized in that:
at least one of $R_6$ to $R_{10}$ is OH and at least one of $R_{6'}$ to $R_{10'}$ is OH, or
at least one of $R_6$ to $R_{10}$ is $N^+(C_1$-$C_4$ alkyl$)_3$, and at least one of $R_{6'}$ to $R_{10'}$ is $N^+(C_1$-$C_4$ alkyl$)_3$, In another particular embodiment, the metal porphyrin complex of formula (I) is characterized in that:
$R_1$ to $R_{10}$ and $R_{1'}$ to $R_{10'}$ are independently H or $N^+(C_1$-$C_4$ alkyl$)_3$, at least one and at most two of $R_1$ to $R_5$ represent $N^+(C_1\text{-}C_4\text{ alkyl})_3$, and at least one and at most two of $R_{1'}$ to $R_{5'}$ represent $N^+(C_1\text{-}C_4\text{ alkyl})_3$.

In another particular embodiment, the metal porphyrin complex of formula (I) is characterized in that:

at least one and at most two of $R_1$ to $R_5$ is OH or $N^+(C_1\text{-}C_4\text{ alkyl})_3$, at least one and at most two of $R_{1'}$ to $R_{5'}$ is OH or $N^+(C_1\text{-}C_4\text{ alkyl})_3$, at least one and at most two of $R_6$ to $R_{10}$ is OH or $N^+(C_1\text{-}C_4\text{ alkyl})_3$, at least one and at most two of $R_{6'}$ to $R_{10'}$ is OH or $N^+(C_1\text{-}C_4\text{ alkyl})_3$, and if at least one of $R_1$ to $R_5$ represents $N^+(C_1\text{-}C_4\text{ alkyl})_3$, then at least one of the other $R_1$ to $R_5$ is selected from the group consisting of H, OH or $C_1\text{-}C_6$ alcohol, and if at least one of $R_{1'}$ to $R_{5'}$ represents $N^+(C_1\text{-}C_4\text{ alkyl})_3$, then at least one of the other $R_{1'}$ to $R_{5'}$ is selected from the group consisting of H, OH or $C_1\text{-}C_6$ alcohol, and if at least one of $R_6$ to $R_{10}$ represents $N^+(C_1\text{-}C_4\text{ alkyl})_3$, then at least one of the other $R_6$ to $R_{10}$ is selected from the group consisting of H, OH or $C_1\text{-}C_6$ alcohol, and if at least one of $R_{6'}$ to $R_{10'}$ represents $N^+(C_1\text{-}C_4\text{ alkyl})_3$, then at least one of the other $R_{6'}$ to $R_{10'}$ is selected from the group consisting of H, OH or $C_1\text{-}C_6$ alcohol.

In a particular embodiment, the metal porphyrin complex of formula (I) is selected from:

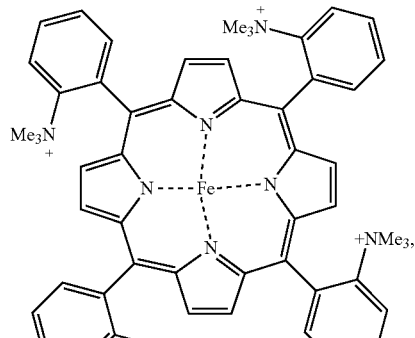

(also called Fe-o-TMA)

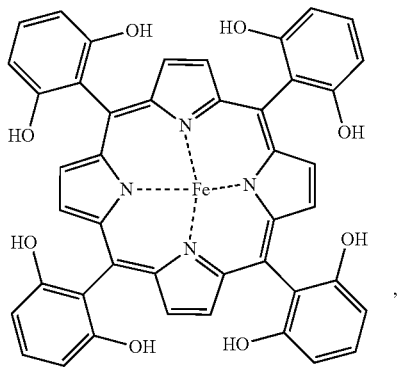

(also called Fe-o-OH or CAT)

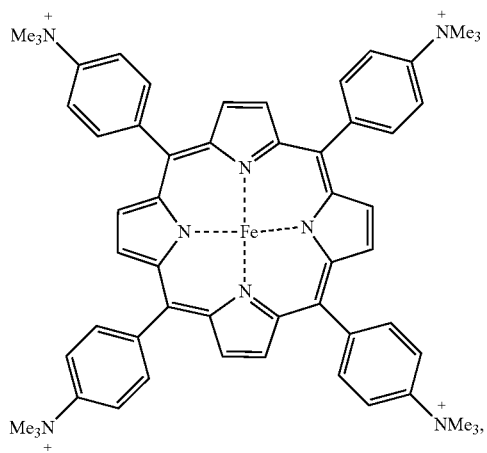

(also called Fe-p-TMA)

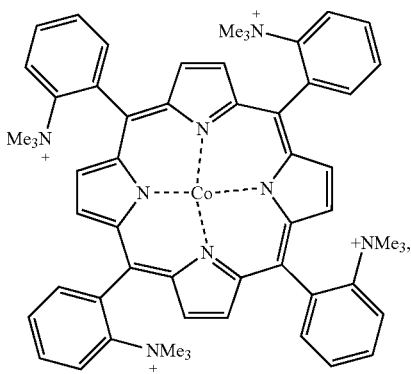

(also called Co-o-TMA)

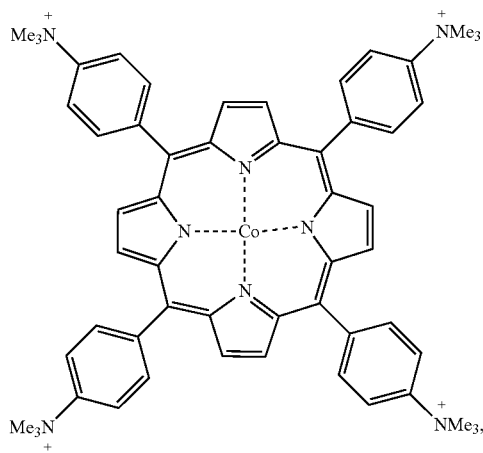

(also called Co-p-TMA)

-continued
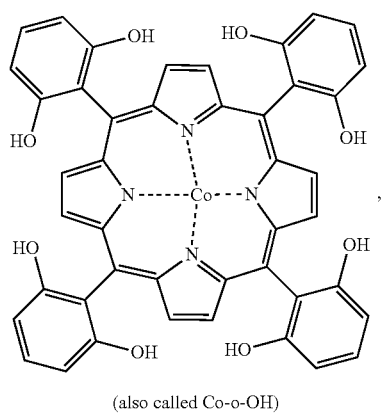
(also called Co-o-OH)
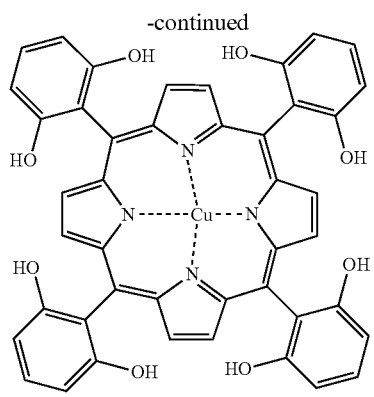
(also called Cu-o-OH)
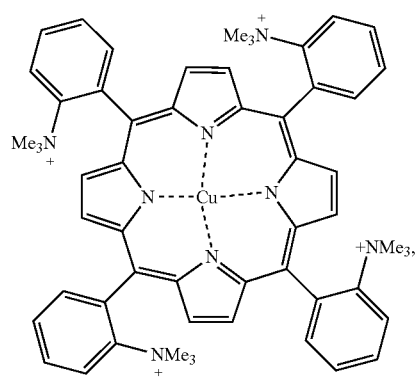
(also called Cu-o-TMA)
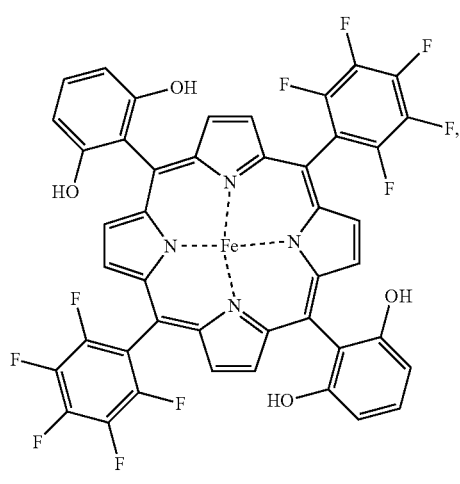
(FCAT)
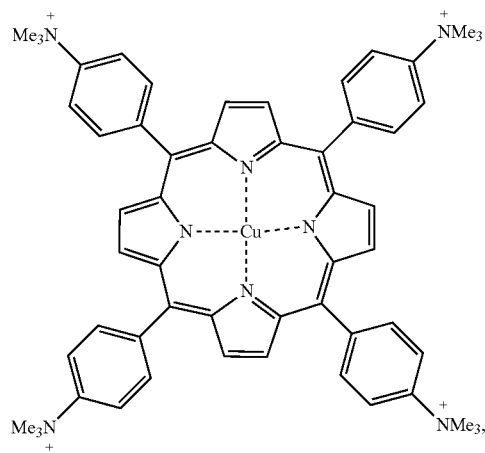
(also called Cu-p-TMA)
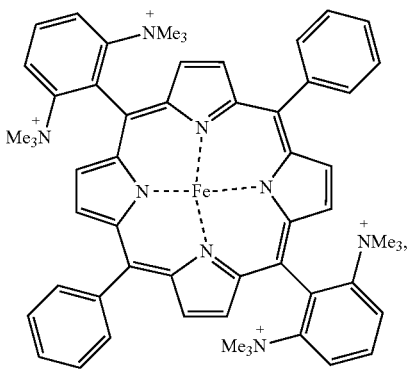

-continued
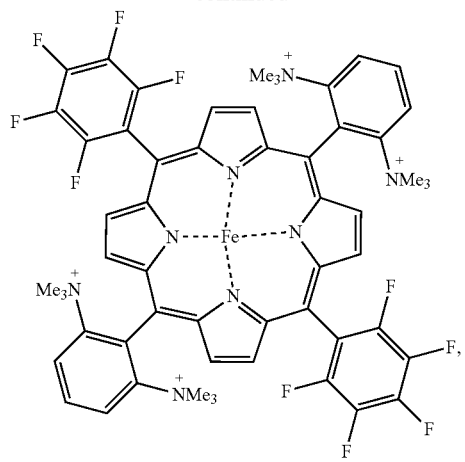
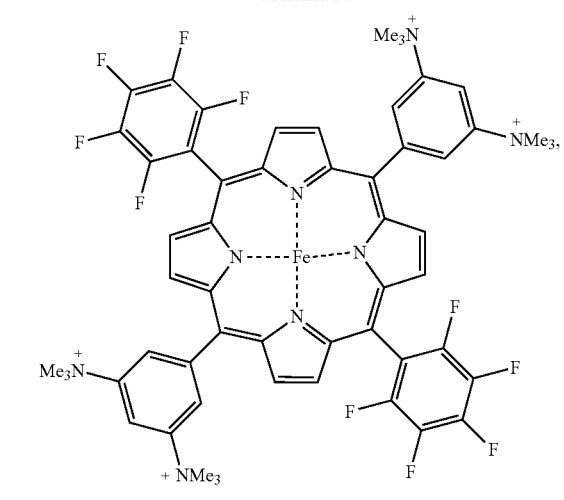
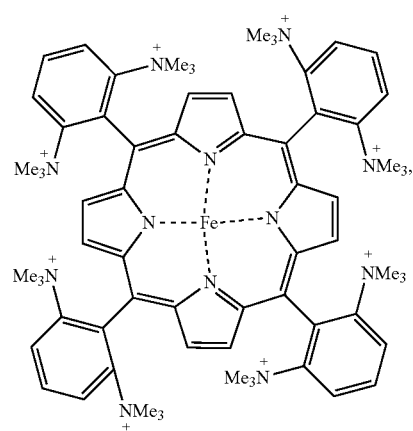
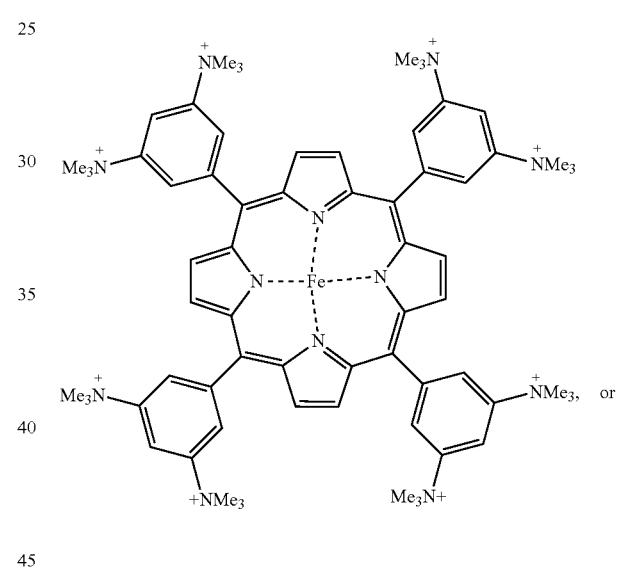
, or
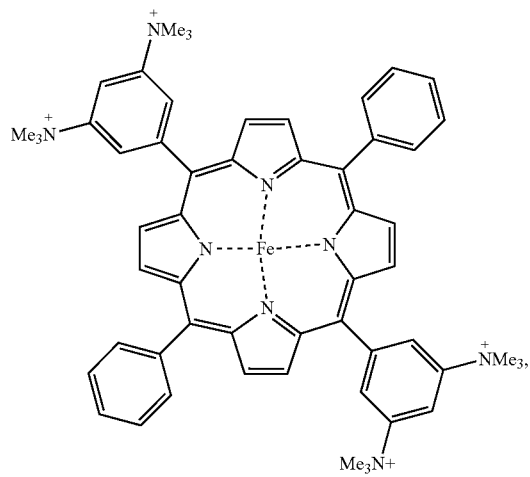
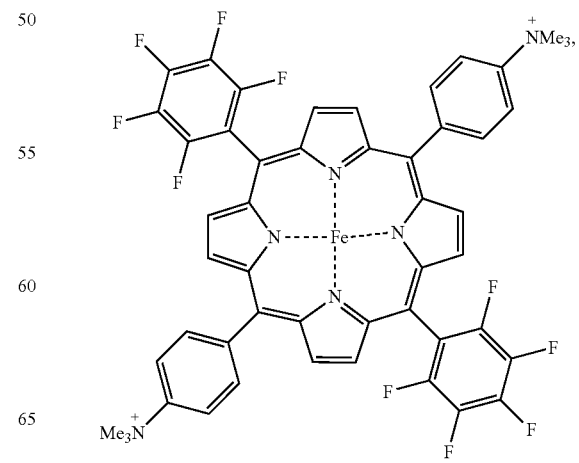

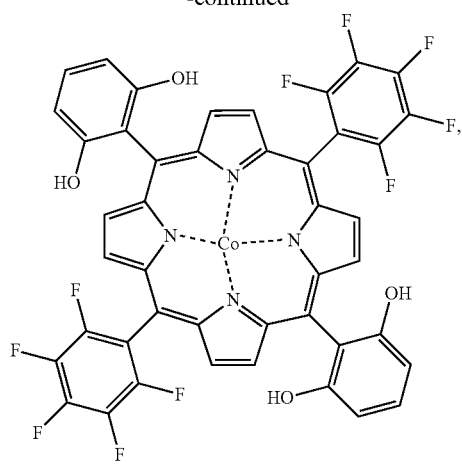
(Co-FCAT)
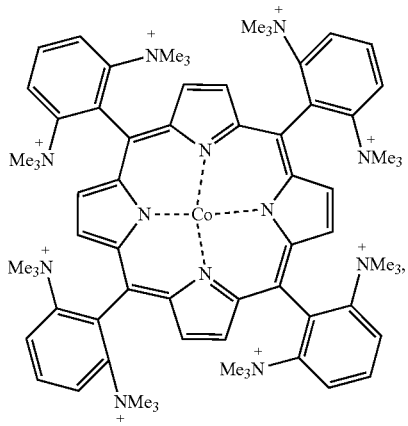
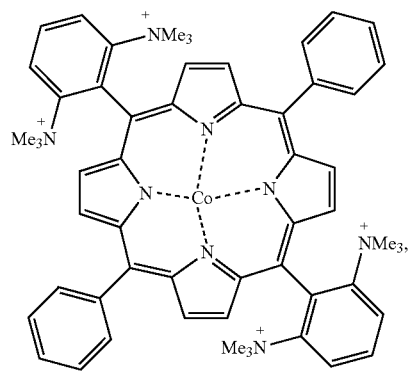
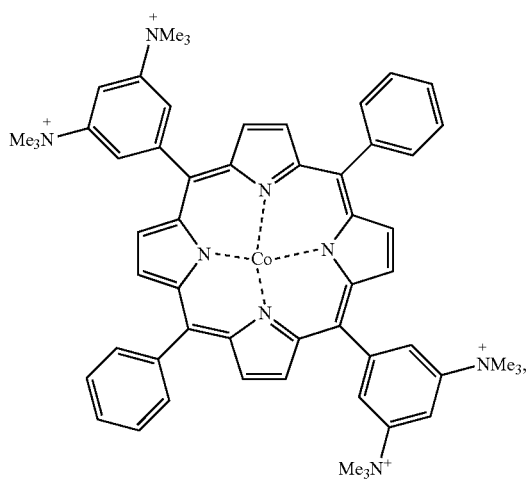
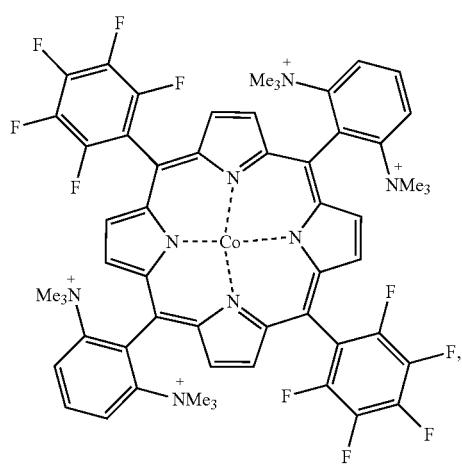
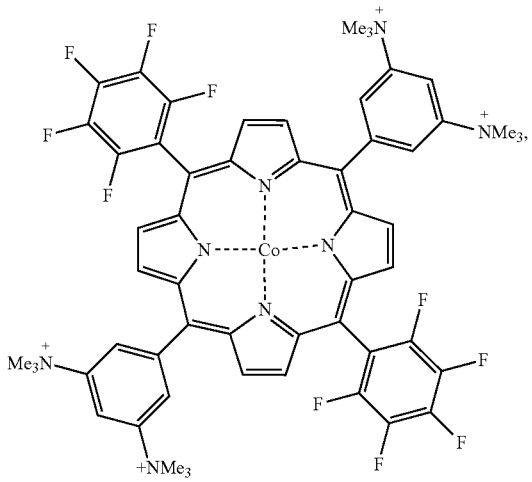

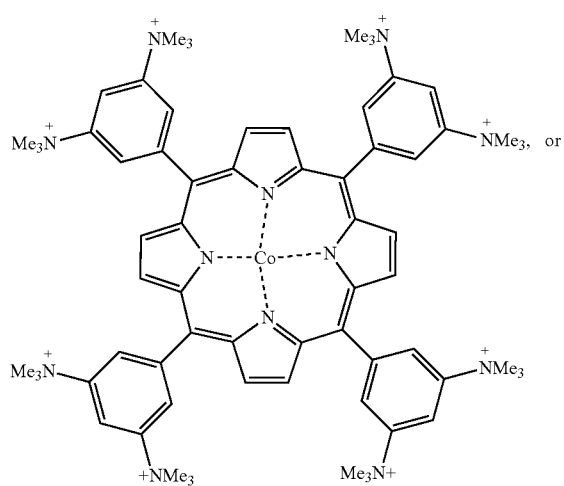
or
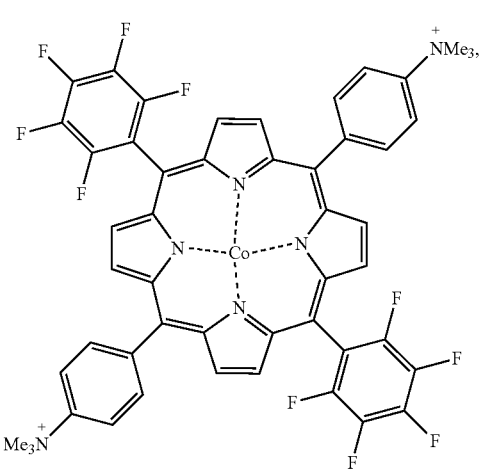
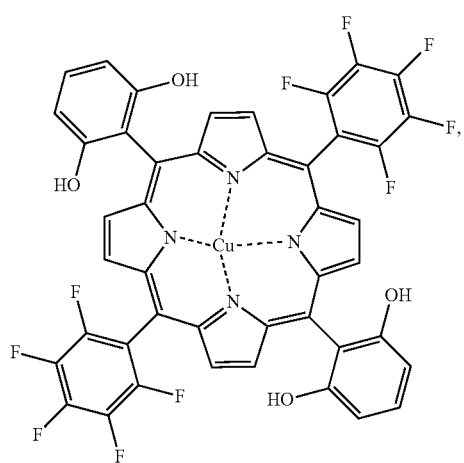
(Cu-FCAT)
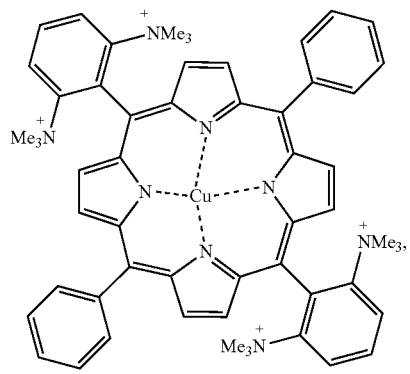
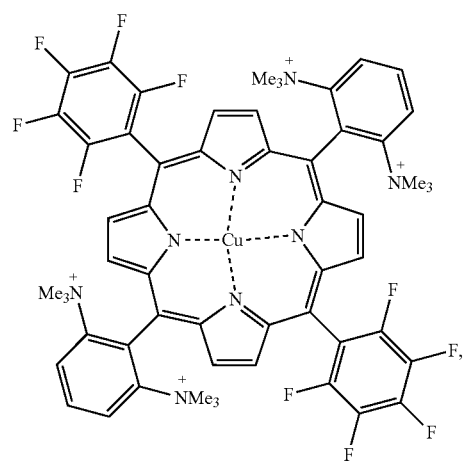
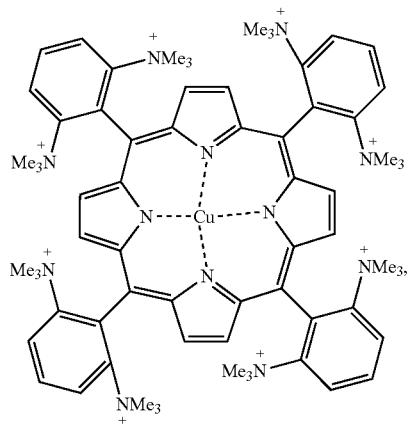

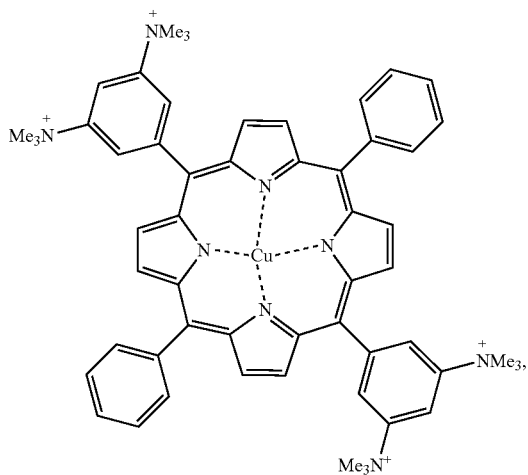

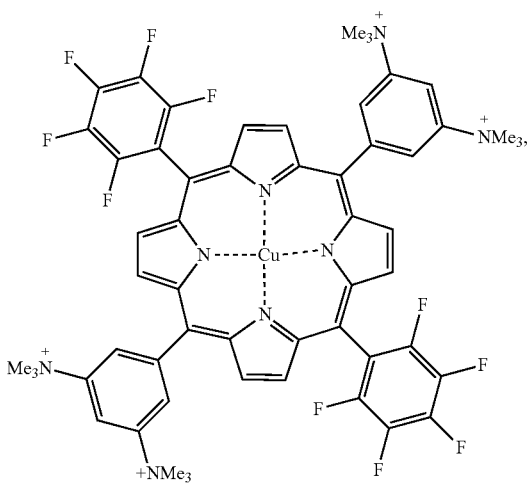

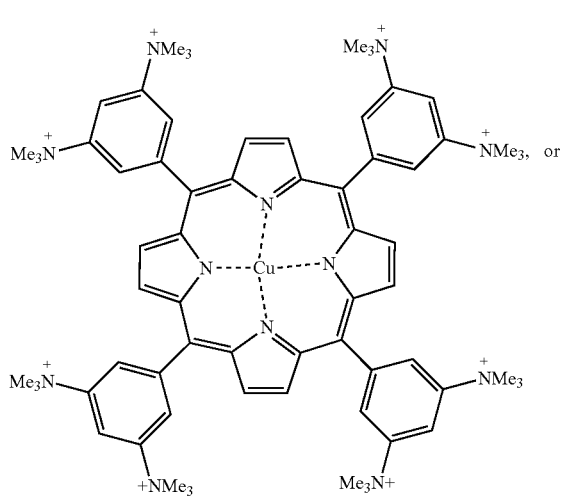

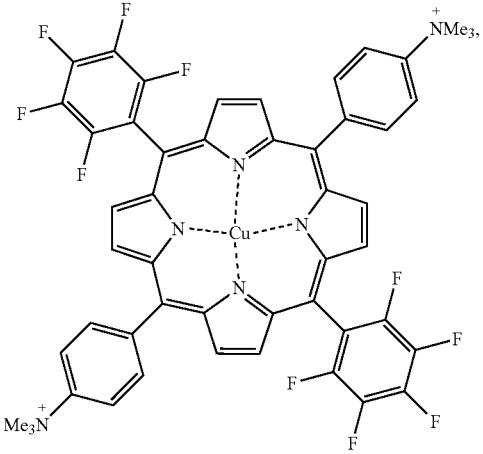

and salts thereof, such as chloride or hexafluorophosphate or triflate salts.

The metal porphyrin complexes of formula (I) are prepared according to methods well-known in the art (see for instance Azcarate et al., *J. Am. Chem. Soc.* 2016, 138, 16639-16644). Of note, when M is Fe, the complex is typically isolated as the Fe(III) complex, and more particularly as the Fe(III)Cl complex of the corresponding porphyrin of formula (I), where appropriate as a salt such as the chloride salt (octachloride, hexachloride, tetrachloride or dichloride depending on the number of anilinium groups in the porphyrin). The active Fe species involved in the catalytic cycle of the reduction of $CO_2$ and/or CO into $CH_4$ are generated in situ in the reaction medium (in particular in the photochemical cell) from the Fe(III) complex, and comprise Fe(0), Fe(I) and Fe(II) species. Therefore, in the present invention, $CO_2$ and/or CO is reduced into $CH_4$ by the porphyrin of formula (I) with Fe(0), Fe(I) and/or Fe(II) (iron at the oxidation state of 0, I or II, respectively). The same is true of complexes with copper or cobalt: the complex is isolated with the metal at a specific oxidation state, which may differ from the oxidation state of the species involved in the catalytic cycle.

Typically, the concentration of the metal porphyrin complex of formula (I) in the photochemical composition is between 1 μM and 50 μM.

1.5. Combinations

In a particular embodiment:
- the sacrificial electron donor is the tertiary amine of formula $NR_1R_2R_3$, in which $R_1$, $R_2$ and $R_3$ are identical or different and each independently selected from a $C_1$-$C_6$ alkyl group optionally substituted with OH, $OC_1$-$C_6$ alkyl, or COOH (advantageously the tertiary amine is triethylamine, triethanolamine, diisopropylethylamine, ethylenediamine tetraacetic acid, preferably triethylamine);
- the photosensitizer is Ir(ppy)$_2$(bpy) or Ir(ppy)$_3$, preferably Ir(ppy)$_3$;
- the metal porphyrin complex is Fe-o-TMA or Fe-p-TMA;
- the solvent is (aqueous, or at least non-anhydrous) acetonitrile; and
- the photochemical composition further comprises phenol or trifluoroethanol (preferably trifluoroethanol) as a proton donor.

Typically, the concentration of the metal porphyrin complex of formula (I) is between 1 μM and 50 μM, the concentration of the photosensitizer is between 50 μM and 1 mM, the concentration of a sacrificial electron donor is between 10 mM and 500 mM, and the concentration of a proton donor in the photochemical composition is between 1 mM and 1 M.

2. Photochemical Cell

The photochemical cell typically comprises at least:
- at least one transparent or at least translucid compartment containing the photochemical composition of the invention, and a gaseous substrate;
- at least one gas inlet and one gas outlet, the gaseous substrate being $CO_2$, CO or a mixture thereof.

The transparent or at least translucid compartment is advantageously made of quartz.

The photochemical cell of the invention may be irradiated by a visible light source able to irradiate the compartment containing the photochemical composition of the invention.

In a particular embodiment, the photochemical cell is saturated with gaseous $CO_2$ and/or CO, that is to say, both the atmosphere and the solution are saturated with gaseous $CO_2$ and/or CO.

The photochemical cell may be used as a closed system regarding $CO_2$ and/or CO gas. This embodiment is of particular interest for a tight control of gas evolution for instance. Conversely, the photochemical cell of the invention may be used in a flow environment (i.e. in a closed environment wherein the atmosphere is controlled but mobile), with a flow of $CO_2$ and/or CO which saturates the photochemical composition of the photochemical cell of the invention. This configuration is particularly useful when industrial production of $CH_4$ is sought for.

Preferably, the photochemical cell does not comprise any gaseous $O_2$, which could have a negative impact on the photochemical reduction of $CO_2$ or CO.

3. Method for Producing Methane ($CH_4$) from $CO_2$ or CO

As explained in detail in the examples below, the production of methane from gaseous $CO_2$ occurs via the intermediate formation of CO.

The method of the invention may thus be implemented using either gaseous CO or gaseous $CO_2$ as starting material.

Furthermore, when using $CO_2$ as starting material, the method may be implemented as a one-pot procedure, or as a two-step procedure, comprising the following successive steps:

1) the formation of CO from $CO_2$ comprising the following successive steps:
   1.a) contacting gaseous $CO_2$ with a photochemical composition of the invention, to obtain a solution comprising dissolved $CO_2$ and/or CO;
   1.b) irradiation of said solution with visible light; and
   1.c) collecting CO; and
2) the formation of $CH_4$ from CO comprising the following successive steps:
   2.a) contacting gaseous CO, with a photochemical composition of the invention, to obtain a solution comprising dissolved CO;
   2.b) irradiation of said solution with visible light; and
   2.c) collecting methane.

When using $CO_2$ as starting material, the partial pressure of $CO_2$—in the photochemical cell—(or more simply the $CO_2$ pressure) may be of less than 1 bar. Alternatively, the $CO_2$ pressure in the catalytic cell may be of 1 bar or more (several bars), such as 2 and 3 bars. In a particular embodiment, the combined partial pressure of CO and $CO_2$ (i.e. the added partial pressure of CO and $CO_2$) may be of less than 1 bar, or may alternatively be of 1 bar or more (several bars), such as 2 and 3 bars.

When using CO as starting material, the partial pressure of CO—in the photochemical cell—(or more simply the CO pressure) may be of less than 1 bar. Alternatively, the CO pressure in the catalytic cell may be of 1 bar or more (several bars), such as 2 and 3 bars.

In a particular embodiment, the method of the invention is performed in a photochemical cell, which is saturated with gaseous $CO_2$ and/or CO, that is to say, both the atmosphere and the solution are saturated with gaseous $CO_2$ and/or CO.

The photochemical cell may be used as a closed system regarding the gaseous substrate ($CO_2$, CO or a mixture thereof). This embodiment is of particular interest for a tight control of gas evolution for instance.

Conversely, the photochemical cell of the invention may be used in a flow environment, with a flow of the gaseous substrate ($CO_2$, CO or a mixture thereof) which saturates the photochemical composition of the photochemical cell of the invention. This configuration is particularly useful when industrial production of $CH_4$ is sought for.

In a particular embodiment, the irradiation lasts several days with wavelength (λ) of 400 nm or more, advantageously for several days, the reaction being stable. In other words, in step b) (or in steps 1b) and 2b)), irradiation occurs at a wavelength of the visible light spectrum, in particular above 420 nm, such as between around 420 nm and around 800 nm, and the solution is irradiated at this or these wavelength(s) for several days, as long as the photochemical composition remains stable. For instance, the solution is irradiated for 4 days, 48 hours or 24 hours.

As used herein, the "yield" of the method for producing $CH_4$ (or CO) gas through photochemical reduction of CO (respectively $CO_2$) gas is the quantum yield of the reduction reaction. The quantum yield is calculated on the basis of the number of incident photons, which is measured for instance using the classical iron ferrioxalate ($K_3Fe(C_2O_4)_3$) chemical actinometer, following the procedure reported in Alsabeh et al. (*Catal. Sci. Technol.* 6, 3623-3630 (2016)) and using the parameters of Montalti, M., Credi, A., Prodi, L. & Gandolfi, M. T. *Handbook of Photochemistry* 3rd edition (CRC Press, 2006) for calculations. The CO-to-$CH_4$ reduction being a six electrons process, the overall quantum yield 0 of the process is determined using the following equation:

$$\Phi(CH_4)\ (\%) = \frac{\text{number of } CH_4 \text{ molecules formed} \times 6}{\text{number of incident photons}} \times 100.$$

Said yield is expressed in %.

The yield of the method is preferably of at least 0.1%, preferably at least 0.15% such as 0.18% or 0.22%.

The selectivity of methane production is preferably of at least 60%, and may even be of 80% or more.

Definitions

As used herein, the words "include," "comprise, "contain", and their variants, are intended to be non-limiting, such that recitation of items in a list is not to the exclusion of other like items that may also be useful in the compositions, devices and methods of this invention.

According to the present invention, an "alkyl" is understood to mean a linear or branched, saturated hydrocarbon chain. Examples of $C_1$-$C_6$ alkyl are methyl, ethyl, n-propyl, i-propyl, n-butyl, s-butyl, t-butyl, pentyl and n-hexyl.

According to the present invention, a "$C_1$-$C_6$ alcohol" is understood to mean a $C_1$-$C_6$ alkyl substituted by at least one hydroxyl group (OH group), preferably only one hydroxyl group. The $C_1$-$C_6$ alcohol may be linear or branched, and is saturated. Preferably, the $C_1$-$C_6$ alcohol is a $C_1$-$C_4$ alcohol. Examples of $C_1$-$C_4$ alcohol are hydroxymethyl, 1-hydroxyethyl, 2-hydroxyethyl, 1-hydroxypropyl, 2-hydroxypropyl, 3-hydroxypropyl, 1-hydroxy-1-methylethyl, 2-hydroxy-1-methylethyl, 1-hydroxybutyl, 2-hydroxybutyl, 3-hydroxybutyl, 4-hydroxybutyl, 1-hydroxy-2-methylpropyl, 2-hydroxy-2-methylpropyl, 3-hydroxy-2-methyl propyl, 1-hydroxy-1-methylpropyl, 2-hydroxy-1-methyl propyl, 3-hydroxy-1-methylpropyl, (hydroxymethyl)-1-propyl, 1,2-dihydroxyethyl.

The term "aromatic group" as used herein alone or as part of another group denotes optionally substituted aromatic groups, monocyclic or bicyclic (fused) groups, containing from 6 to 10 carbons in the ring portion, such as phenyl, naphthyl and indenyl. Phenyl and naphthyl are the more preferred aromatic groups.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 to 3 heteroatoms preferably selected from O, N and S (preferably N) in the ring, and may be bonded to the remainder of the molecule through a carbon or heteroatom. Exemplary heteroaromatics include furyl, thiophenyl, pyrrolyl, isoxazolyl, oxazolyl, isothiazolyl, thiazolyl, imidazolyl, triazolyl, pyridyl, pyrimidinyl, pyrazinyl, pyridazinyl, indolyl, isoxindolyl, chromene-2-onyle (or coumarinyl), benzoxazolyl, benzothiazolyl, benzotriazolyl, quinolinyl, or isoquinolinyl and the like. Preferably, the heteroaromatic group is a pyridine, a quinoline or an isoquinoline.

The term "biaryl group" as used herein denotes an Ar—Ar'-group wherein Ar and Ar' are identical or different and each independently represent a 5- to 10-membered monocyclic or bicyclic aromatic or heteroaromatic group. Preferably, Ar and Ar' are identical or different and each independently represent a 6-membered monocyclic aromatic or heteroaromatic group, such as phenyl or pyridine. A preferred biaryl group is biphenyl.

As used herein, a "transition metal" is understood as any non-radioactive element in the d-block of the periodic table, which includes groups 3 to 12 on the periodic table, as well as lanthanides elements. Preferably, transition metals only encompass elements from groups 3 to 12 of the periodic table. Preferred transition metals include Co, Cu, Fe, Ni, Ru, Rh, Pd, Ag, Au, Ir, Pt, Mo, Cr or Mn.

As used herein, the "TurnOver Number (TON)" is practically defined as the number of catalytic cycles per catalyst amount: Mol number of $H_2$, CO and $CH_4$ were determined by converting peak integrations from GC measurements into moles in the sample headspace thanks to individual calibration curves taking into account the irradiated sample volume.

As used herein, the "TurnOver Frequency (TOF)" refers to the turnover per unit of time:

$$TOF = \frac{TON}{t},$$

with t representing the time of catalysis.

As used herein, the acronym NHE is understood as "Normal Hydrogen Electrode".

As used herein, the acronym SCE is understood as "Saturated Calomel Electrode".

EXAMPLES

Figure 1:
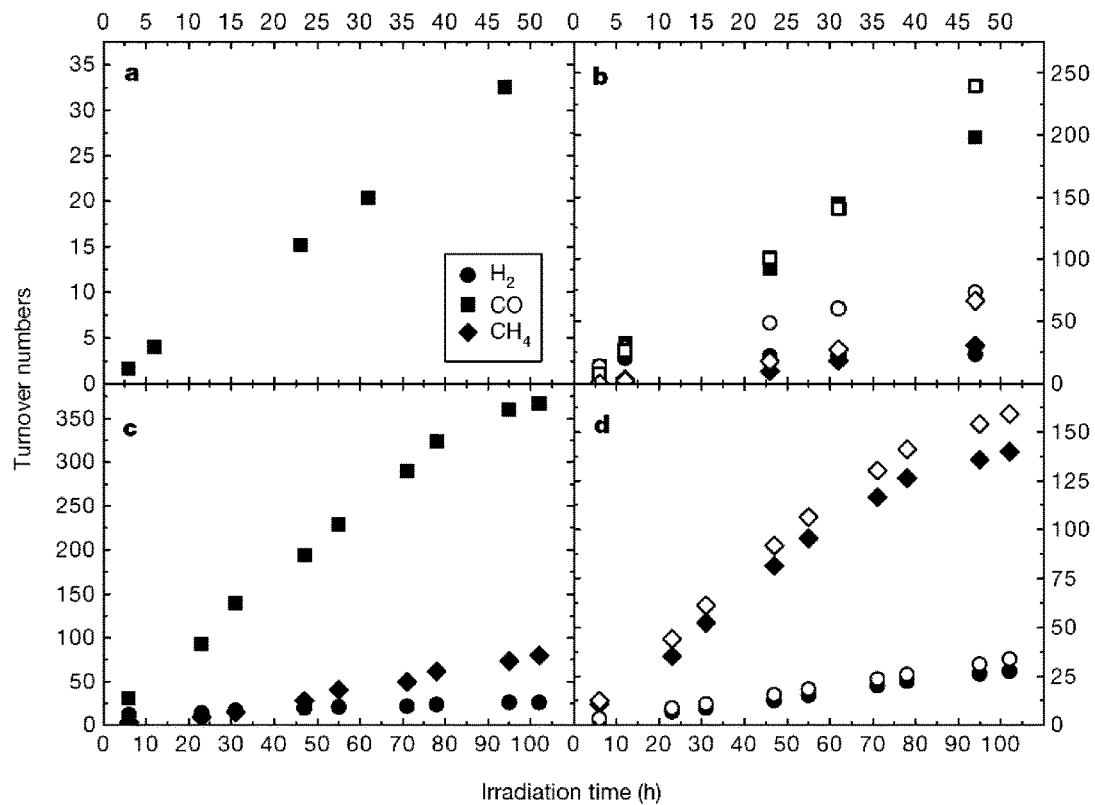
FIG. 1. Photochemical reduction of $CO_2$ under visible light irradiation. Shown is the formation of gaseous products (in terms of turnover numbers, TONs) as a function of irradiation time, using an acetonitrile solution saturated with 1 atm $CO_2$ (a, b, c) or 1 atm CO (d) and containing 2 μM of catalyst chloro Fe-p-TMA and 50 mM of TEA. a, With no sensitizer, only CO is produced. b, When 0.2 mM of sensitizer Ir(ppy)$_3$ is present, $H_2$, CO and $CH_4$ are produced (filled symbols); adding 0.1 M of TFE increases their production rate (open symbols). c, $H_2$, CO and $CH_4$ product evolution over an extended irradiation time in the presence of 0.2 mM of Ir(ppy)$_3$. d, Under a CO atmosphere and with 0.2 mM of sensitizer Ir(ppy)$_3$ present, $H_2$ and $CH_4$ are produced (filled symbols); adding 0.1 M of TFE increases their production rate (open symbols). Data points in FIG. 2 are the results of at least two individual experiments. Typical uncertainty on TON values is ca. 5%, corresponding to the size of data points.

The following examples are meant for illustrative purposes only, and shall not be construed as limitative in any way.

Materials and Methods

Synthesis of Catalysts Chloro Fe-p-TMA, Chloro Fe-o-TMA and Chloro Fe-o-OH.

The synthesis of chloro iron(III) 5,10,15,20-tetra(4-N,N,N-trimethylanilinium)porphyrin (chloro Fe-p-TMA), chloro iron(III) 5,10,15,20-tetra(2-N,N,N-trimethylanilinium)porphyrin (chloro Fe-o-TMA) and chloro iron(III) 5,10,15,20-tetrakis(2',6'-dihydroxyphenyl) porphyrin (chloro Fe-o-OH) have been described (see respectively Costentin et al. *Proc. Natl. Acad. Sci. U.S.A.* 112, 6882-6886 (2015) and Costentin et al. *Science* 338, 90-94 (2012)).

Synthesis of Catalysts Chloro Co-p-TMA, Chloro Cu-o-TMA and Chloro Cu-o-OH chloro cobalt(III) 5,10,15,20-tetra(4-N,N,N-trimethylanilinium)porphyrin (chloro Co-p-TMA), chloro copper(II) 5,10,15,20-tetra(2-N,N,N-trimethylanilinium)porphyrin (chloro Cu-o-TMA) and chloro copper(II) 5,10,15,20-tetrakis(2',6'-dihydroxyphenyl) porphyrin (chloro Cu-o-OH) were synthesized using the protocols described in Costentin et al. *Proc. Natl. Acad. Sci. U.S.A.* 112, 6882-6886 (2015) and Costentin et al. *Science* 338, 90-94 (2012), replacing $FeCl_3$ respectively by $CoCl_3$ and $CuCl_2$.

Photochemical Measurements.

Irradiations of acetonitrile (99.9% extra-dry, Acros Organics) solutions containing triethylamine (99% pure, Acros Organics) as sacrificial electron donor, and fac-(tris-(2-phenylpyridine))iridium(III) ($Ir(ppy)_3$, 99%, Aldrich) as sensitizer were realized in a closed 1×1 cm quartz suprasil cuvette (Helima 117.100F-QS) equipped with a home-designed headspace glassware. Solutions were saturated with argon (>99.998%, Air Liquide), $^{12}CO_2$ (>99.7%, Air Liquide), $^{13}CO_2$ (99% atom $^{13}$C, Aldrich) or $^{12}C_0$ (>99.997%, Air Liquide) for 20 minutes before irradiation. A Newport LCS-100 solar simulator, equipped with an AM1.5 G standard filter allowing 1 Sun irradiance, was used as the light source combined with a Schott GG420 longpass filter and 2 cm long glass OS cell filled with deionized water to prevent catalyst absorbance and to cut off IR and low UV.

Spectrophotometric Measurements.

UV-Visible absorption data were collected with an Analytik Jena Specord 600 UV/Vis spectrophotometer. Emission quenching measurements were conducted with a Cary Eclipse fluorescence spectrophotometer (Agilent Technologies), with the excitation wavelength set at 420 nm and the emission spectrum measured between 430 and 700 nm. Emission intensities used for the Stern-Volmer analysis were taken at 517 nm, i.e. the emission maximum of $Ir(ppy)_3$. The lifetime of the emissive excited state of $Ir(ppy)_3$ was taken as 1.9 μs as reported by Dedeian et al. (*Inorg. Chem.* 30, 1685-1687 (1991)).

Reduction Products Analysis.

Gaseous products analysis was performed with an Agilent Technology 7820A GC system equipped with a capillary column (CarboPLOT P7, length 25 m, inner diameter 25 mm) and a thermal conductivity detector. Calibration curves for $H_2$, CO and $CH_4$ were established separately. Control experiments, with no catalyst, no $CO_2$ or no light were conducted in the same conditions than the full system. Ionic chromatography measurements were performed with a Thermo Scientific Dionex ICS-1100 system. Mass spectra were obtained by a ThermoFisher Scientific TRACE Ultra gas chromatograph equipped with a CP 7514 column (Agilent Technologies) and coupled to a DSQ II mass spectrometer in positive ionisation mode, using a TriPlus headspace autosampler.

Ton Calculation.

Turnover number is practically defined as the number of catalytic cycles per catalyst amount. Mol number of $H_2$, CO and $CH_4$ were determined by converting peak integrations from GC measurements into moles in the sample headspace thanks to individual calibration curves taking into account the irradiated sample volume (3.5 mL).

Quantum Yield Calculation.

Using the method described above, based on three independent measurements, the number of incident photons to the sample was determined to be $(2.18\pm0.17)\times10^{19}$ photons per hour. Taking 195 as the highest TON number for $CH_4$ (Table 1, entry 13), a quantum yield Φ of ca. 0.22% after 102 hours of irradiation is obtained.

Results

The results are summarized in table 1 below.

TABLE 1

Summary of the reaction conditions used for evaluating the catalytic performance of catalysts chloro Fe-p-TMA and chloro Fe-o-OH. The solvent is acetonitrile.

| Experiment n° | [Fe-p-TMA] μM | Gas | [Ir(ppy)₃] mM | [TEA] mM | λ nm | Time | TONs CO | CH₄ | H₂ |
|---|---|---|---|---|---|---|---|---|---|
| 1 | 2 | CO₂ | — | 50 | >420 | 47 | 33 | — | — |
| 2 | 2 | CO₂ | 0.2 | 50 | >420 | 47 | 198 | 31 | 24 |
| 3 (in the presence of 0.1M TFE) | 2 | CO₂ | 0.2 | 50 | >420 | 47 | 240 | 66 | 73 |
| 4 | 2 | CO₂ | 0.2 | 50 | >420 | 102 | 367 | 79 | 26 |
| 5 | 2 | Argon | 0.2 | 50 | >420 | 47 | — | — | 43 |
| 6 | — | CO₂ | 0.2 | 50 | >420 | 47 | 3 | — | 1 |
| 7 | 2 | CO₂ | 0.2 | — | >420 | 23 | 5 | — | — |

TABLE 1-continued

Summary of the reaction conditions used for evaluating the catalytic performance of catalysts chloro Fe-p-TMA and chloro Fe-o-OH. The solvent is acetonitrile.

| Experiment n° | [Fe-p-TMA] μM | Gas | [Ir(ppy)$_3$] mM | [TEA] mM | λ nm | Time | TONs CO | CH$_4$ | H$_2$ |
|---|---|---|---|---|---|---|---|---|---|
| 8 | 2 | CO$_2$ | 0.2 | 50 | dark | 23 | — | — | — |
| 9 (Fe-o-OH used instead of Fe-p-TMA) | 2 | CO$_2$ | 0.2 | 50 | >420 | 47 | 139 | 26 | 15 |
| 10 | 2 | CO | 0.2 | 50 | >420 | 47 | — | 89 | 18 |
| 11 | 2 | CO | 0.2 | 50 | >420 | 102 | — | 140 | 28 |
| 12 (in the presence of 0.1M TFE) | 2 | CO | 0.2 | 50 | >420 | 102 | — | 159 | 34 |
| 13 (in the presence of 0.5M TFE) | 2 | CO | 0.2 | 50 | >420 | 102 | — | 195 | 45 |
| 14 | — | CO | 0.2 | 50 | >420 | 47 | — | — | — |
| 15 | 2 | CO | 0.2 | 50 | dark | 23 | — | — | — |

Methane formation was also observed under the conditions of entry 2 or 10, replacing catalyst chloro Fe-p-TMA by chloro Fe-o-TMA, chloro Co-p-TMA, and Cu-o-OH.

Finally, 3 experiments were performed using compound:

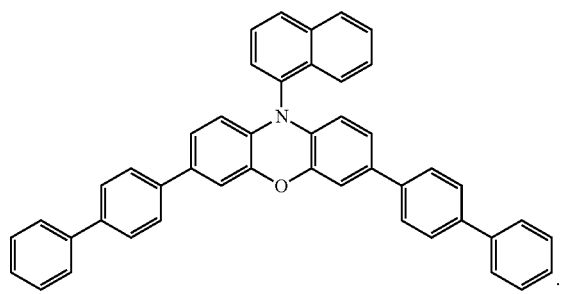

(hereinafter phen4) as photosensitizer

Figure 6:
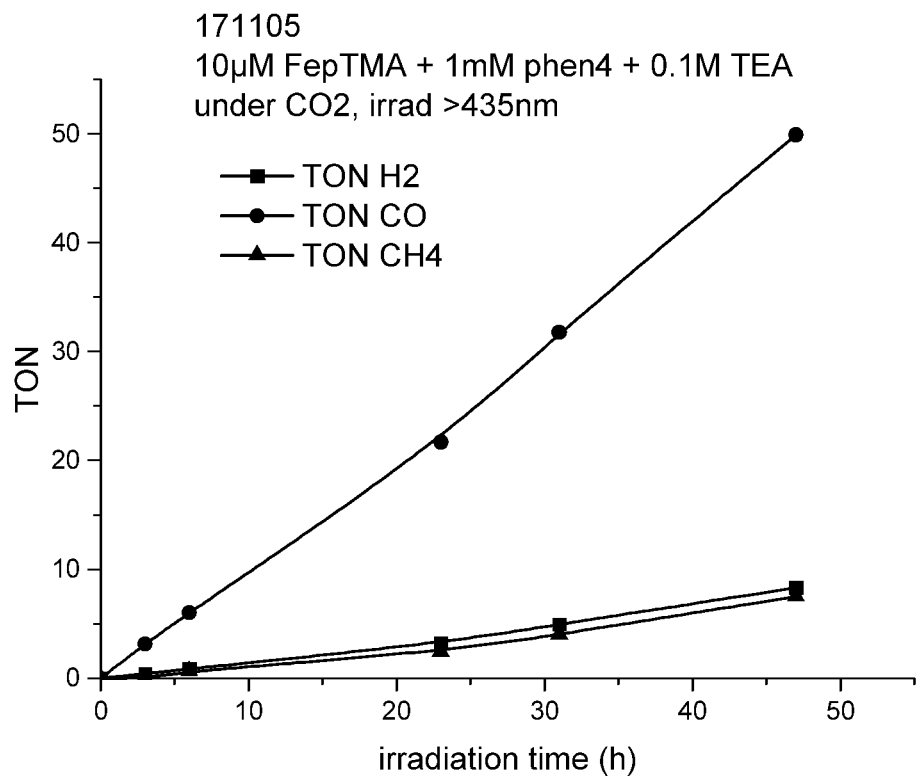
FIG. 6. Evolution of the TON with time. The reaction conditions are those described for experiment 16 (see Table 2 below).
Figure 7:
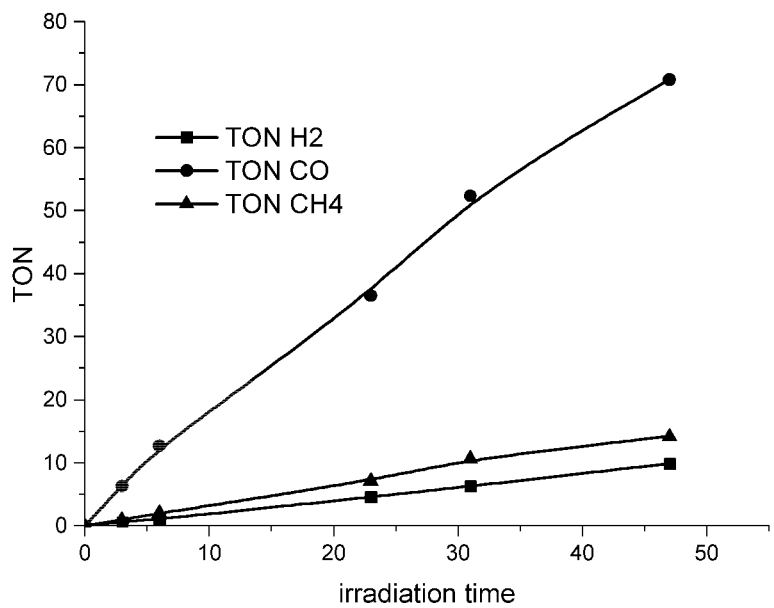
FIG. 7. Evolution of the TON with time. The reaction conditions are those described for experiment 17(see Table 2 below).
Figure 8:
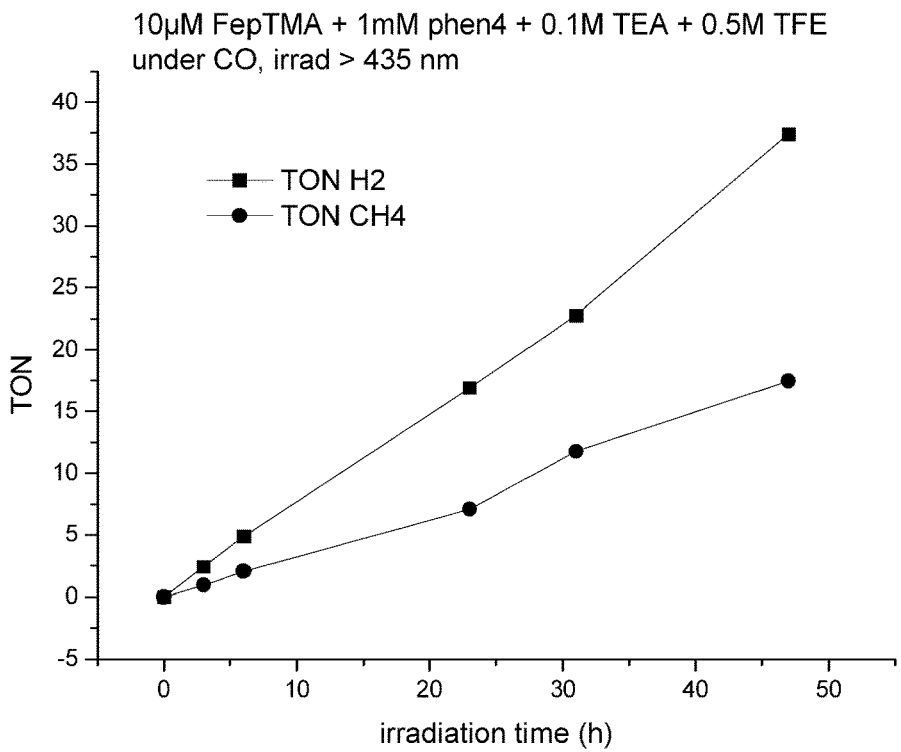
FIG. 8. Evolution of the TON with time. The reaction conditions are those described for experiment 18 (see Table 2 below).
Figure 9:
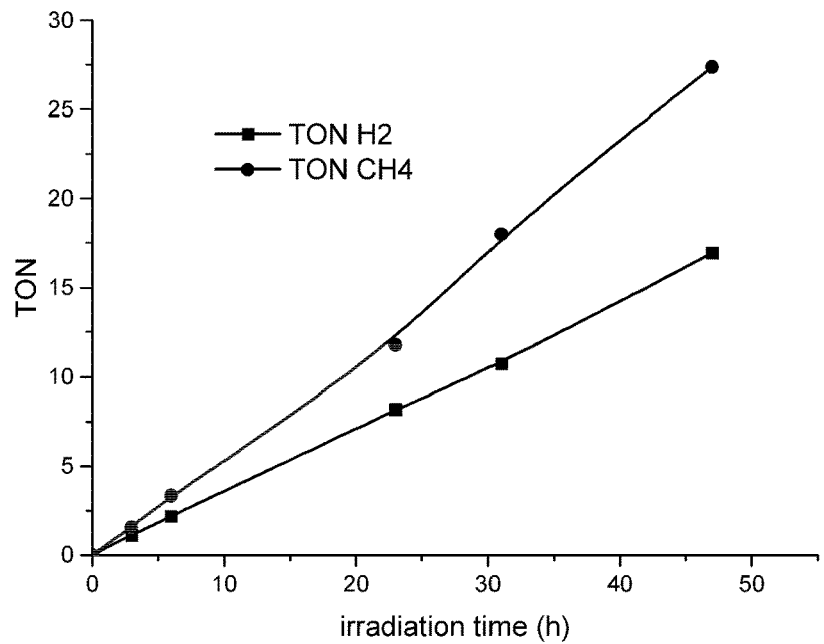
FIG. 9. Evolution of the TON with time. The reaction conditions are those described for experiment 19 (see Table 2 below).
Figure 10:
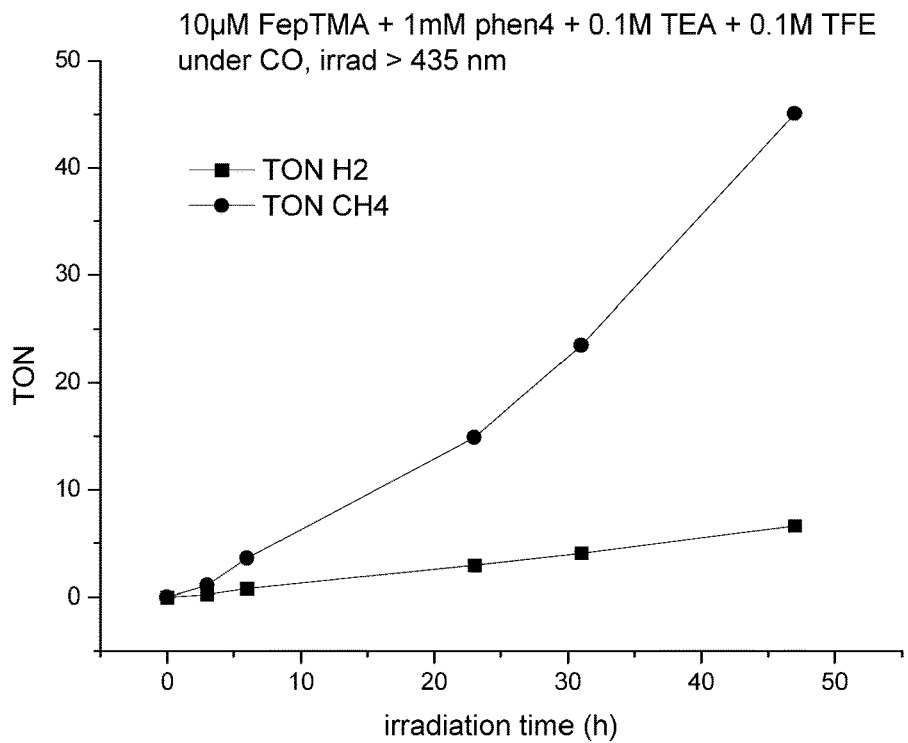
FIG. 10. Evolution of the TON with time. The reaction conditions are those described for experiment 20 (see Table 2 below).
Figure 11:
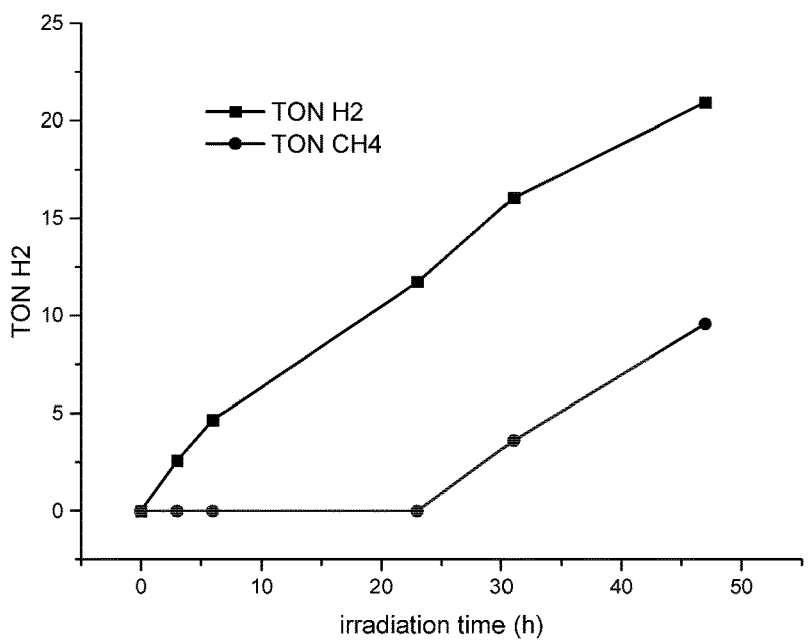
FIG. 11. Evolution of the TON with time. The reaction conditions are those described for experiment 21 (see Table 2 below).

The experimental conditions are summarized in Table 2, and in FIG. 6 (experiment 16), FIG. 7 (experiment 17), FIG. 8 (experiment 18), FIG. 9 (experiment 19), FIG. 10 (experiment 20), FIG. 11 (experiment 21).

Discussion

Chloro Fe-p-TMA was firstly used as a photocatalyst without a photosensitizer under visible light irradiation (λ>420 nm) with triethylamine (TEA, 50 mM) as sacrificial electron donor. Illumination of a 1 atm CO$_2$-saturated solution of acetonitrile (ACN) containing 2 μM of Fe-p-TMA at room temperature for 47 h selectively produced CO, with a turnover number (TON) in CO relative to catalyst concentration of 33. No side products were observed, and the linear production of CO with time indicates good stability of the catalytic system.

A factor that can potentially limit the catalytic rate of this system is the 3-electron reduction of the initial Fe$^{III}$ porphyrin species to generate the active Fe$^0$ state. Using electron donors with high reducing ability was envisioned to be favourable, and adding 0.2 mM of Ir(ppy)$_3$ (Table 1) as photosensitizer (E$^0$(Ir(ppy)$_3^+$/Ir(ppy)$_3$*≈−1.73 V vs. SCE and e(Ir(ppy)$_3$/Ir(ppy)$_3^-$≈−2.19 V vs. SCE) to the solution indeed enhanced the photochemical CO$_2$ reduction, so that 47 h of irradiation gave a TON in CO relative to chloro Fe-p-TMA of 198 (Table 1, entry 2 and FIG. 1b). Adding 0.1 M trifluoroethanol (TFE, Table 1, entry 3) slightly increased the TON further to 240, likely due to TFE facilitating the

TABLE 2

Summary of the reaction conditions used for evaluating the catalytic performance of catalysts chloro Fe-p-TMA and chloro Fe-p-OH. The solvent is dimethylformamide (DMF).

| Experiment n° | [Fe-p-TMA] μM | Gas | [phen4] mM | λ mM | Time nm | h | TONs CO | CH$_4$ | H$_2$ |
|---|---|---|---|---|---|---|---|---|---|
| 16 | 10 | CO$_2$ | 1 | 100 | >435 | 47 | 50 | 8 | 8 |
| 17 (in the presence of 0.1M TFE) | 10 | CO$_2$ | 1 | 100 | >435 | 47 | 71 | 14 | 10 |
| 18 (in the presence of 0.5M TFE) | 10 | CO | 1 | 100 | >435 | 47 | — | 17 | 37 |
| 19 (in the presence of 0.25M TFE) | 10 | CO | 1 | 100 | >435 | 47 | — | 27 | 17 |
| 20 (in the presence of 0.1M TFE) | 10 | CO | 1 | 100 | >435 | 47 | — | 45 | 7 |
| 21 | 10 | CO | 1 | 100 | >435 | 47 | — | 10 | 20 |

C—O bond cleavage step. With the photosensitizer, products included not only CO but also 10% hydrogen and 12% methane that correspond to TONs of 24 and 31 (Table 1, entry 2 and FIG. 1b). No other gaseous product was formed, and analysis of the liquid phase failed to detect methanol or formaldehyde by $^1$H NMR or formate (HCOO$^-$) by ion chromatography. The presence of 0.1 M of TFE increased the selectivities (and TONs) for H$_2$ and CH$_4$ to 19% (73) and 18% (66), respectively (Table 1, entry 3 and FIG. 1b). Blank experiments (Table 1, entries 1, 5-8) confirmed that no methane is formed in the absence of sensitizer, CO$_2$, catalyst, electron donor or light.

Figure 2:
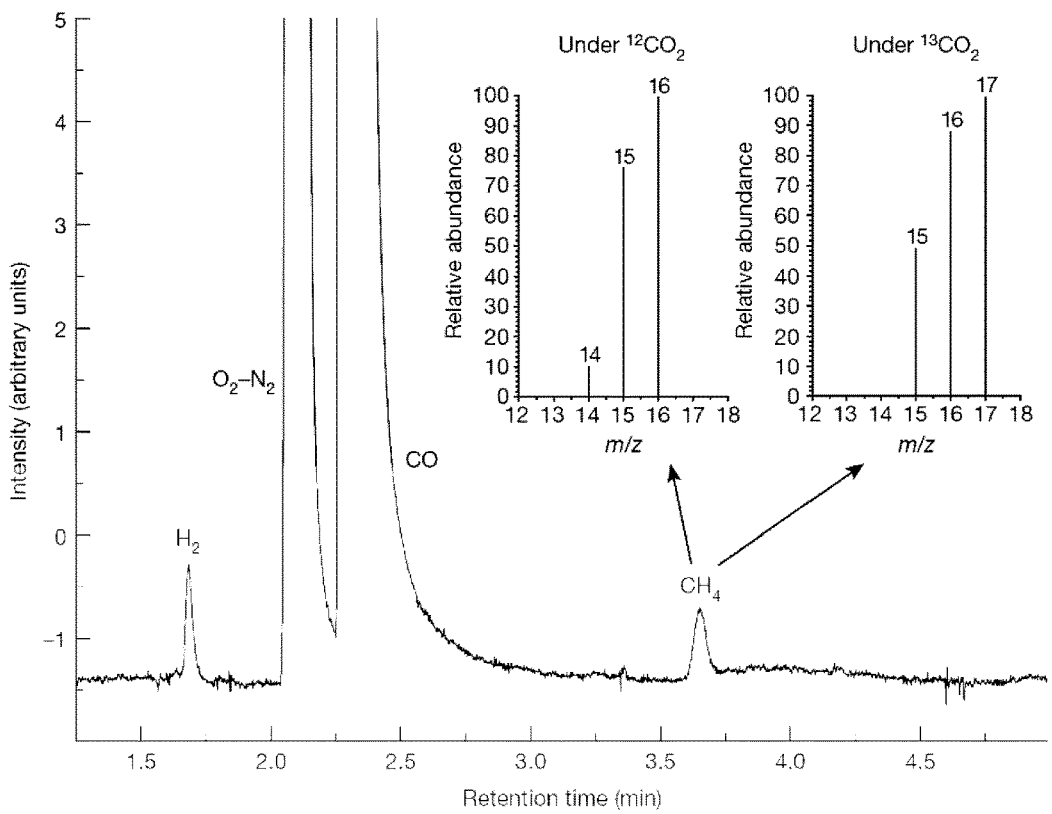
FIG. 2. Methane detection. Typical gas chromatogram observed during long-term irradiation of a solution containing 2 μM of catalyst chloro Fe-p-TMA, 50 mM of TEA and 0.2 mM of sensitizer Ir(ppy)$_3$, under $^{12}CO_2$ or $^{13}CO_2$ atmosphere. Inset, Mass spectra of methane generated under a $^{12}CO_2$ or $^{13}CO_2$ atmosphere.
Figure 4:
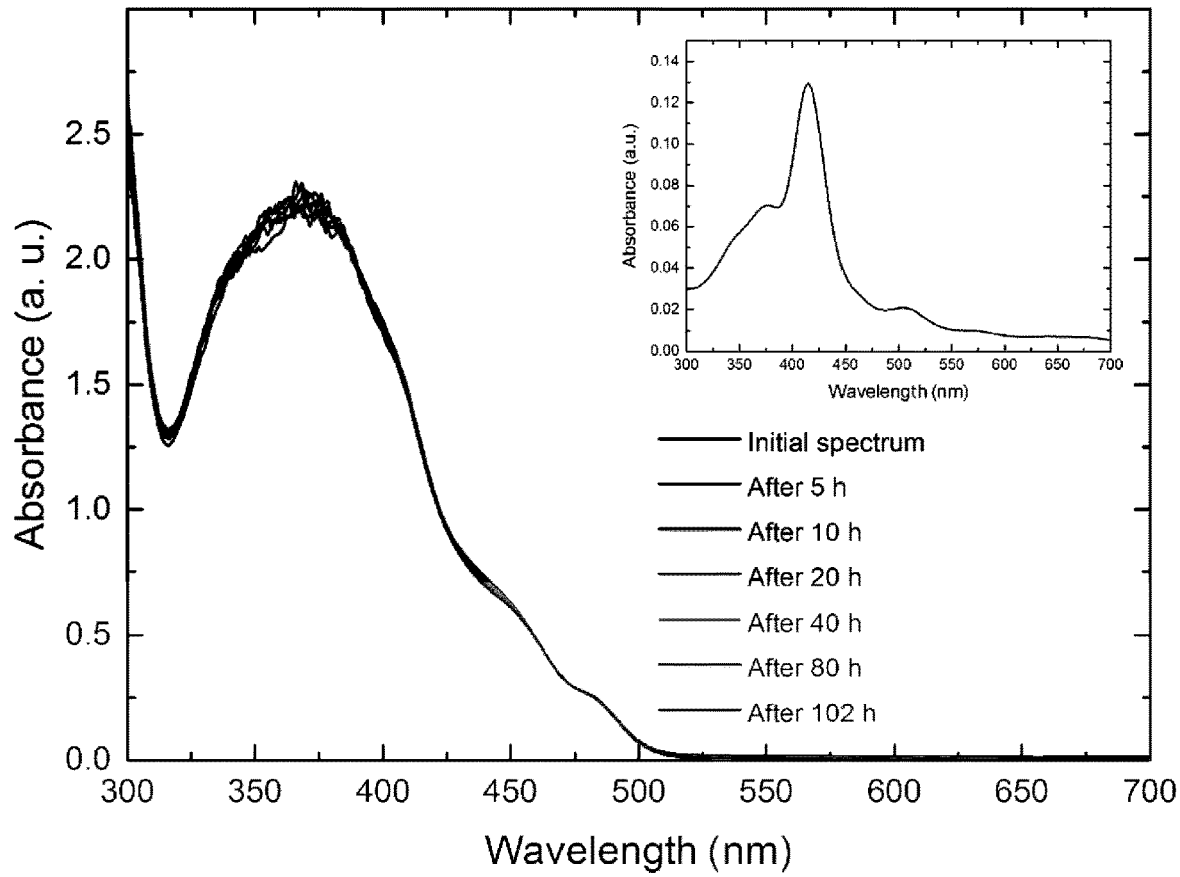
FIG. 4. Evolution of the absorption spectrum with time. The absorption spectrum of a $CO_2$-saturated ACN solution containing 2 μM of chloro Fe-p-TMA, 0.2 mM of Ir(ppy)$_3$, 0.05 M of TEA upon visible (>420 nm) light irradiation remains stable over the course of experiments, highlighting the stability of the system. Inset, absorption spectrum of 2 μM of catalyst Fe-p-TMA in ACN (no sensitizer Ir(ppy)$_3$), showing that in the photochemical mix, >90% of photons above 420 nm are absorbed by Ir(ppy)$_3$.

In isotope labelling experiments conducted under a $^{12}$CO$_2$ or a $^{13}$CO$_2$ atmosphere, GC-MS analysis (FIG. 2) identified as reaction product $^{12}$CH$_4$ (m/z=16) or $^{13}$CH$_4$ (m/z=17), respectively, confirming that methane originates from CO$_2$ reduction. Increasing the irradiation time increased the amount of CO$_2$ reduction products generated (FIG. 1c). The longest irradiation time of 102 h produced CO, CH$_4$ and H$_2$ with TONs (and selectivities) of 367 (78%), 79 (17%) and 26 (5%) respectively (Table 1, entry 4 and FIG. 1c). These values correspond to a methane production rate of 763 μmol per hour and per gram of catalyst (μmol/h/g), which exceeds the rate of many other catalysts that generate methane from CO$_2$. The linear evolution of both CO and CH$_4$ over more than 80 h and the stable absorption spectrum of the system under irradiation (FIG. 4), with no evidence for degradation of the sensitizer Ir(ppy)$_3$ or catalyst chloro Fe-p-TMA, illustrate the stability of the catalytic system.

Evolution of the different products (FIG. 1c) shows that methane production only starts after a significant amount of CO has built up, suggesting that CO is an intermediate in the methane formation process. It was previously shown by UV-Vis spectroscopy that irradiation of a CO$_2$ saturated solution of chloro Fe-p-TMA without a sensitizer (in that case only CO is obtained) led to the formation of detectable amount of Fe$^{II}$CO species. It may thus be hypothesized that this iron-carbonyl adduct is an intermediate for further reduction towards methane in the presence of a strong reducing agent. Experiments were thus conducted in a 1 atmosphere CO-saturated acetonitrile solution under visible light irradiation (λ>420 nm), with Ir(ppy)$_3$ as sensitizer and TEA as sacrificial electron donor (FIG. 1d). In a 47 h irradiation experiment, this slightly lowered H$_2$ production and increased by almost a factor of 3 CH$_4$ production compared to the experiment using a CO$_2$-saturated solution: 83% of product was CH$_4$ and 17% H$_2$ (Table 1, entry 10), with the CH$_4$ formation rate of 1865 μmol/h/g. Blank experiments in the absence of Fe-p-TMA or in the absence of light did not give any reduction product (Table 1, entries 13 and 14), while a longer irradiation time of 102 h enhanced the selectivity for methane further to 87% (Table 1, entry 11 and FIG. 1d). Addition of a weak acid in moderate concentration (TFE 0.1 M) slightly increased the methane formation rate (from a TON of 140 to 159) with some loss of selectivity (from 87% to 82%, Table 1, entry 12). The successful methane evolution under these conditions over 102 h with an average rate of 1467 μmol/h/g illustrate the robustness, activity and selectivity of the photochemical system. Optimized concentration for TFE (0.5 M) led to a TON of 195 for methane with 81% selectivity (Table 1, entry 13).

When replacing chloro Fe-p-TMA by chloro Fe-o-OH, methane was also evolved although in slightly smaller amounts (26 TON after 47 h irradiation and 14% CS, Table 1, entry 9). The standard redox potential $E^0(Fe^I/Fe^0)=-1.575$ V vs. SCE[26] in DMF (dimethylformamide) for chloro Fe-o-OH is only 75 mV more negative than that of Fe-p-TMA, and as in the latter case, the substituents on the phenyls may help stabilizing reaction intermediates (through internal H bonds involving the —OH groups). In contrast, the non-substituted tetraphenyl Fe porphyrin (chloro FeTPP, Table 1) only gives CO and H$_2$ (with TONs/selectivities of 84/79% and 22/21%, respectively) under the same irradiation conditions, likely due to its significantly more negative standard redox potentials (e.g. $E^0(Fe^I/Fe^0)=-1.67$ V vs. SCE in DMF) and the absence of phenyl ring substituents for stabilizing intermediate species involved in hydrocarbon production. The ability to produce methane is thus not restricted to catalyst chloro Fe-p-TMA, but is likely a more general property of Fe porphyrins that have a sufficiently positive standard redox potential and are functionalized with substituents that can stabilize intermediates involved in the catalytic cycle.

Figure 3:
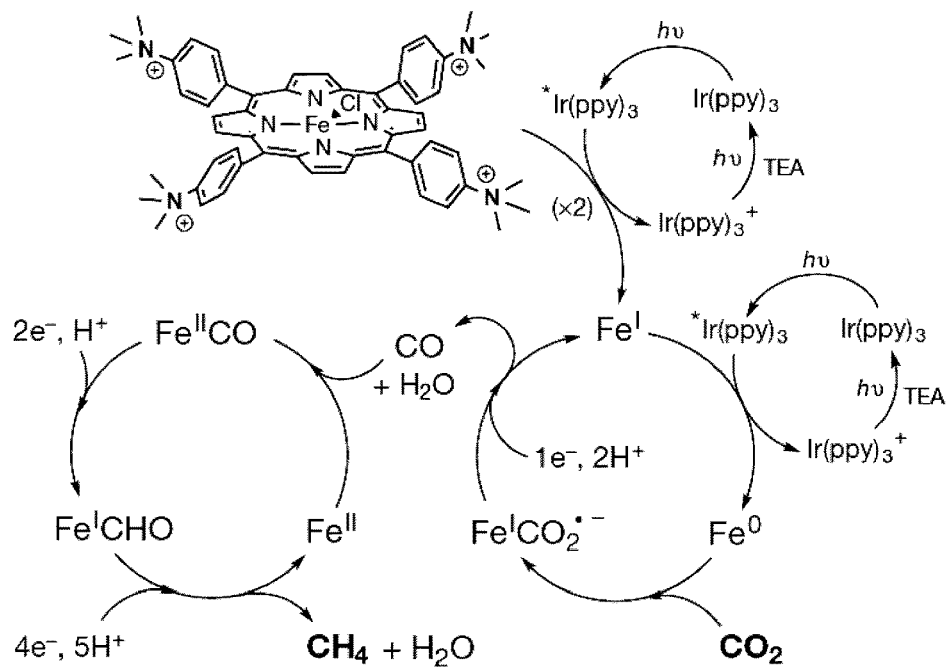
FIG. 3. Sketch of the proposed mechanism for $CO_2$ reduction to $CH_4$ by catalyst Fe-p-TMA. Initially, the starting $Fe^{III}$ porphyrin (shown at top left) is reduced with three electrons to the catalytically active $Fe^0$ species (top part of the scheme). The $Fe^0$ species reduces $CO_2$, with the resultant $Fe^I$ regenerated through electron transfer from the excited photosensitizer (right-hand side cycle). The CO produced binds to $Fe^{II}$ and is further reduced with a total of six electrons (transferred from the excited sensitizer) and six protons to generate methane, via a postulated $Fe^I$-formyl ($Fe^I$CHO) intermediate (left-hand side cycle).
Figure 5:
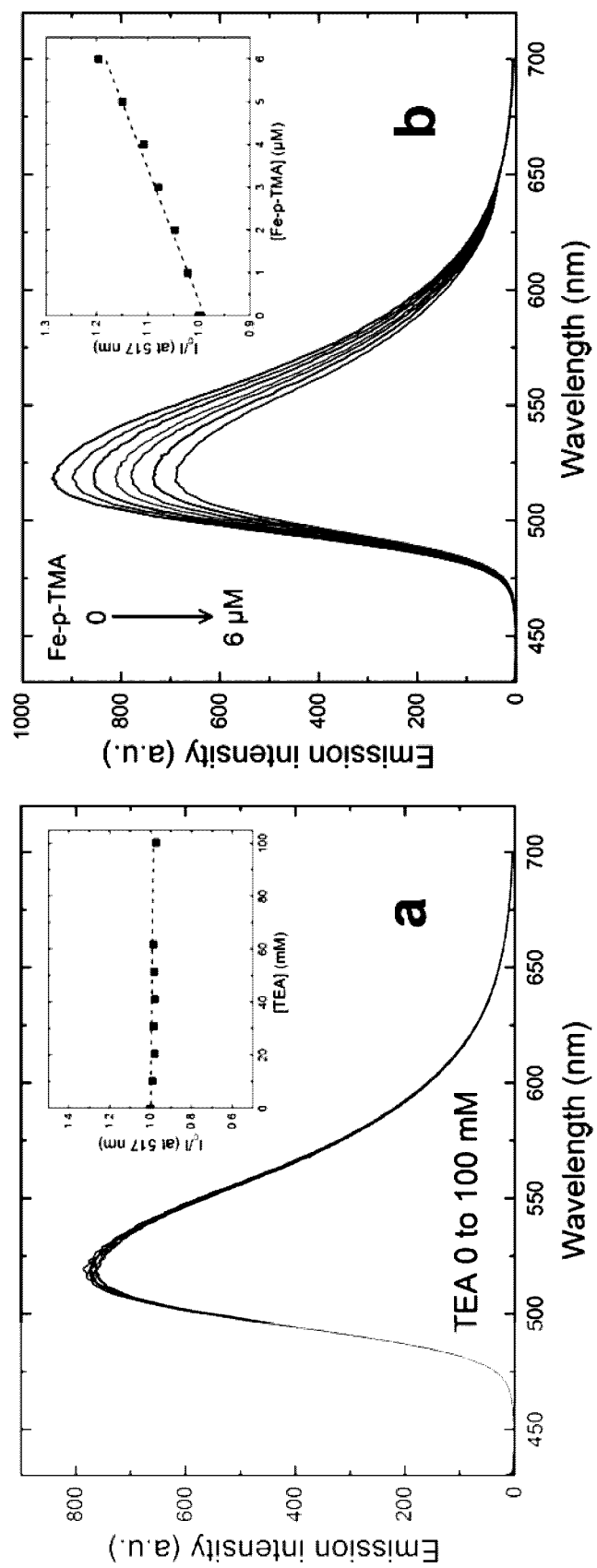
FIG. 5. Sensitizer emission quenching after excitation at 420 nm. a, Upon increasing concentration of TEA in a 0.1 mM ACN solution of Ir(ppy)$_3$, no emission quenching is observed, as confirmed by the Stern-Volmer analysis (inset). b, Upon increasing concentration of chloro Fe-p-TMA in a 0.2 mM ACN solution of Ir(ppy)$_3$, emission quenching is observed corresponding to a diffusion-controlled quenching rate of $(1.7\pm0.1)\times10^{10}$ $M^{-1}$ $s^{-1}$ as determined by Stern-Volmer analysis (inset).

Another parameter for CO$_2$ reduction beyond the two-electrons production of CO is the driving force for charge transfer from the excited state of the sensitizer. When replacing Ir(ppy)$_3$ by the less reducing ruthenium complex Ru(bpy)$_3^{2+}$ ($E^0$(Ru(bpy)$_3^{2+}$/Ru(bpy)$_3^+$)≈−1.33 V vs. SCE and $E^0$(Ru(bpy)$_3^{3+}$/Ru(bpy)$_3^{2+*}$)=−0.81 V vs. SCE), only CO and H$_2$ and no CH$_4$ were obtained, possibly because the Ru excited state or its reduced form are not able to trigger the carbonyl reduction from the Fe$^{II}$CO adduct. Emission quenching experiments between Ir(ppy)$_3$* and chloro Fe-p-TMA on one hand and Ir(ppy)$_3$* and TEA on the other hand revealed very weak quenching in the latter case while it is very efficient, diffusion-controlled, in the former case ($k_q$≈1.7×10$^{10}$ M$^{-1}$ s$^{-1}$, FIG. 5), suggesting that direct electron transfer occurs from the excited sensitizer Ir(ppy)$_3$ to the Fe porphyrin. This is in line with the standard redox potential value of the excited iridium complex ($E^0$(Ir(ppy)$_3^+$/Ir(ppy)$_3$*)≈1.73 V vs. SCE), which is more negative than all three redox couples related to the Fe porphyrin (Fe$^{III}$/Fe$^{II}$, Fe$^{II}$/Fe$^I$ and Fe$^I$/Fe$^0$). After electron transfer, the oxidized Ir(ppy)$_3^+$ is reduced by the sacrificial electron donor TEA upon irradiation, thereby closing the catalytic cycle and generating the protonated triethylamine TEAH$^+$ that could then act as proton donor as seen before. FIG. 3 sketches a plausible mechanism based on these considerations, which involves a postulated formyl intermediate that may be stabilized by through-space interactions between the positive charges of the trimethylammonio groups and the partial negative charge on the CHO species bound to the metal. With complete reduction of the Fe$^{II}$CO adduct necessitating six electrons, the quantum yield for CH$_4$ formation is Φ=0.22%.

The generality of the reaction to other metal (Cobalt and Copper) porphyrins was also demonstrated. It was also shown that the photosensitizer is not restricted to metal complexes, and that organic photosensitizers may also be used. Finally, it has been showed that aprotic solvent could be mixed with high content water (up to 70% in acetonitrile) for producing CH$_4$.

The invention claimed is:

1. A photochemical composition for producing methane by reducing at least one of CO$_2$ and CO at visible light, comprising:
    a solution comprising an organic solvent,
    a sacrificial electron donor;
    a proton donor having a pKa in acetonitrile greater than or equal to 28;
    a photosensitizer whose reduced state has a standard redox potential more negative than −1.45 V vs Saturated Calomel Electrode, wherein the photosensitizer is a complex of a transition metal with at least two 2-phenylpyridine (ppy) ligand; and
a metal porphyrin complex of formula (I):

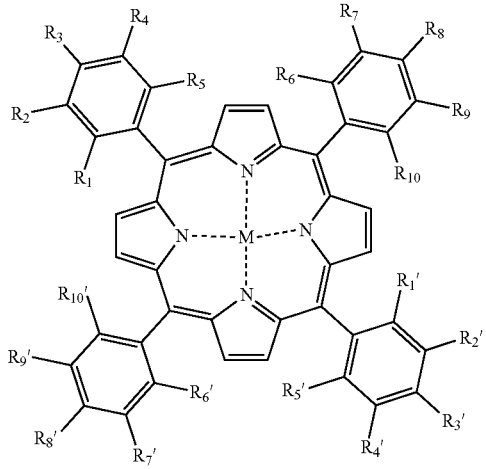

(I)

wherein:
M represents a transition metal ion,
$R_1$ to $R_{10}$ and $R_1'$ to $R_{10}'$ are independently selected from the group consisting of H, OH, F, $C_1$-$C_6$ alcohol, and $N^+(C_1$-$C_4$ alkyl$)_3$,
and wherein:
at least one of $R_1$ to $R_5$ is OH and at least one of $R_1'$ to $R_5'$ is OH, or
at least one of $R_1$ to $R_5$ is $N^+(C_1$-$C_4$ alkyl$)_3$, and at least one of $R_1'$ to $R_5'$ is $N^+(C_1$-$C_4$ alkyl$)_3$,
and salts thereof.

2. The photochemical composition of claim 1, wherein the photosensitizer having a standard redox potential more negative than $-1.35$ V vs Saturated Calomel Electrode in the reduced state is a metal complex of formula (III):

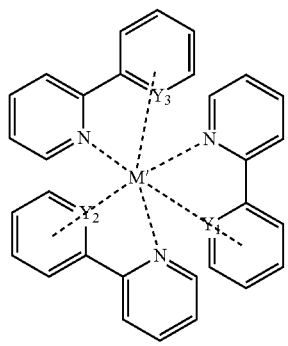

(III)

wherein $Y_1$, $Y_2$ and $Y_3$ are $CH_2$, and M' represents a transition metal.

3. The photochemical composition of claim 1, wherein the concentration of photosensitizer in the photochemical composition is of between 50 mM and 1 mM.

4. The photochemical composition of claim 1, wherein the concentration of sacrificial electron donor in the photochemical composition is of between 10 mM and 500 mM.

5. The photochemical composition of claim 1, wherein the sacrificial electron donor is a tertiary amine.

6. The photochemical composition of claim 5, wherein the tertiary amine is:
of formula $NR_1R_2R_3$, in which $R_1$, $R_2$ and $R_3$ are identical or different and each independently selected from a $C_1$-$C_6$ alkyl group optionally substituted with OH, $OC_1$-$C_6$ alkyl, or COOH; or
of formula (IV):

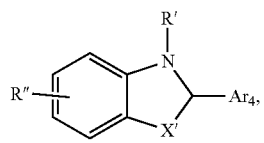

(IV)

wherein
X' is O or NR, with R representing a $(C_1$-$C_4)$alkyl,
R' is a $(C_1$-$C_4)$ alkyl,
R" is a hydrogen, halogen, CN, or a $(C_1$-$C_4)$ alkyl, and
$Ar_4$ is selected from a monocyclic or bicyclic 5- to 10-membered aromatic or heteroaromatic ring, optionally substituted by a halogen, CN, OH, a biaryl group or a monocyclic 5- or 6-membered aromatic or heteroaromatic ring, said monocyclic 5- or 6-membered aromatic or heteroaromatic ring being optionally substituted by a halogen, CN, OH.

7. The photochemical composition of claim 1, wherein the proton donor is phenol or trifluoroethanol.

8. The photochemical composition of claim 1, wherein the metal porphyrin complex of formula (I) comprises at least two $N^+(C_1$-$C_4$ alkyl$)_3$ groups.

9. The photochemical composition of claim 1, wherein, in the metal porphyrin complex of formula (I):
at least one of $R_6$ to $R_{10}$ is OH and at least one of $R_6'$ to $R_{10}'$ is OH, or
at least one of $R_6$ to $R_{10}$ is $N^+(C_1$-$C_4$ alkyl$)_3$, and at least one of $R_6'$ to $R_{10}'$ is $N^+(C_1$-$C_4$ alkyl$)_3$.

10. The photochemical composition of claim 1, wherein in the metal porphyrin complex of formula (I):
$R_1$ to $R_{10}$ and $R_1'$ to $R_{10}'$ are independently H or $N^+(C_1$-$C_4$ alkyl$)_3$,
at least one and at most two of $R_1$ to $R_5$ represent $N^+(C_1$-$C_4$ alkyl$)_3$, and
at least one and at most two of $R_1'$ to $R_5'$ represent $N^+(C_1$-$C_4$ alkyl$)_3$.

11. The photochemical composition of claim 1, wherein the metal porphyrin complex of formula (I) is selected from:

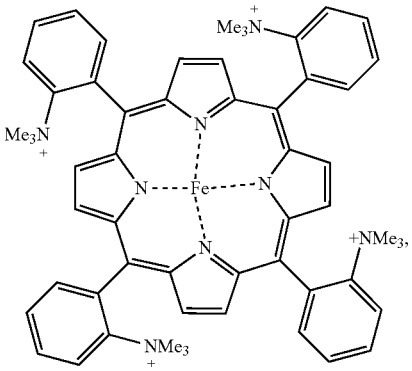

31
-continued
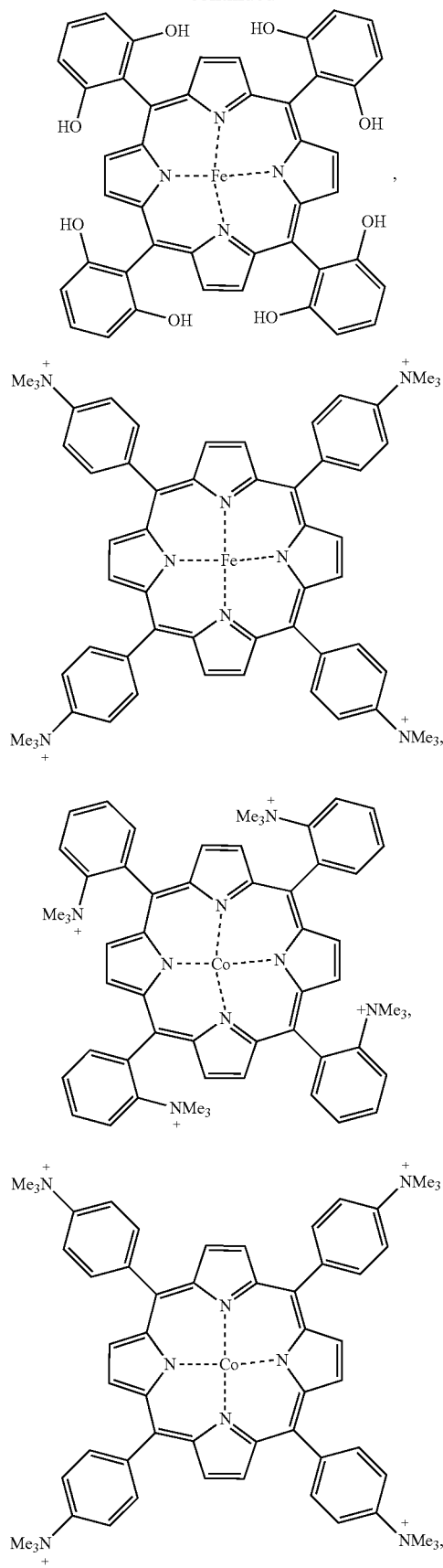
32
-continued
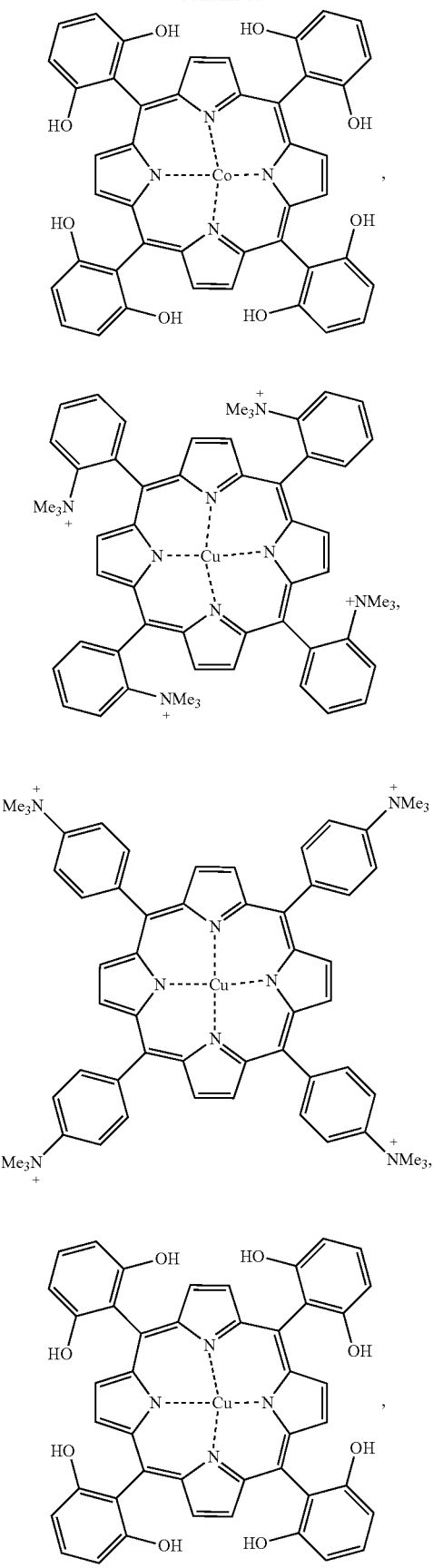

33
-continued
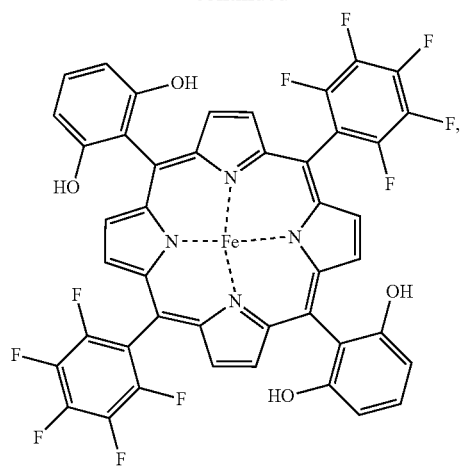
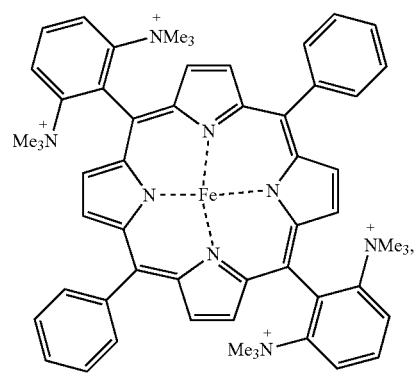
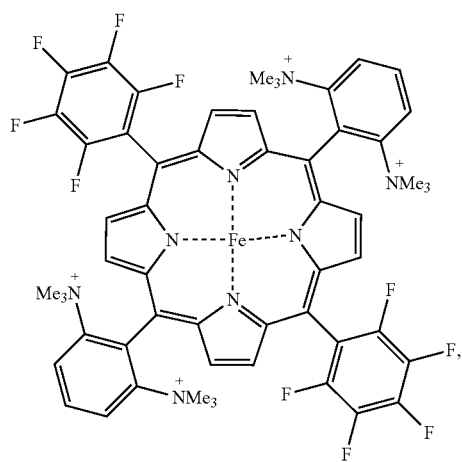
34
-continued
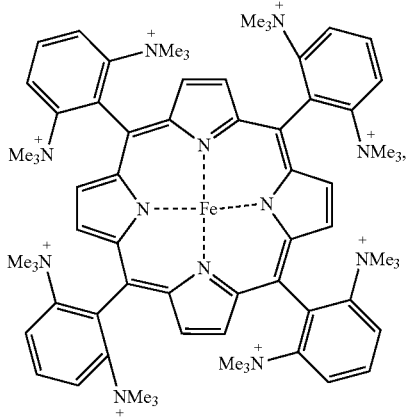
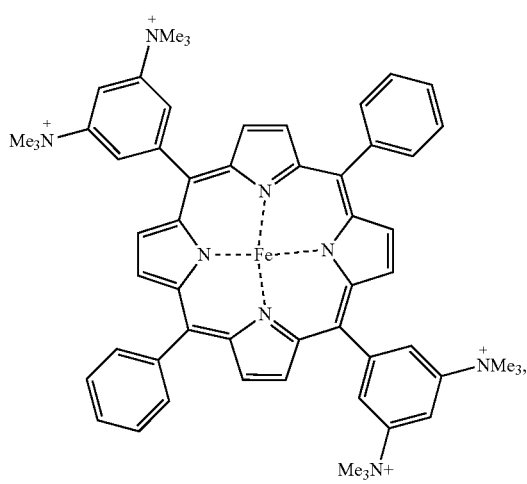
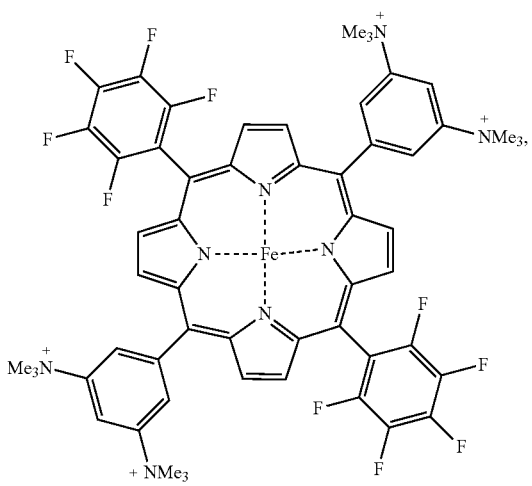

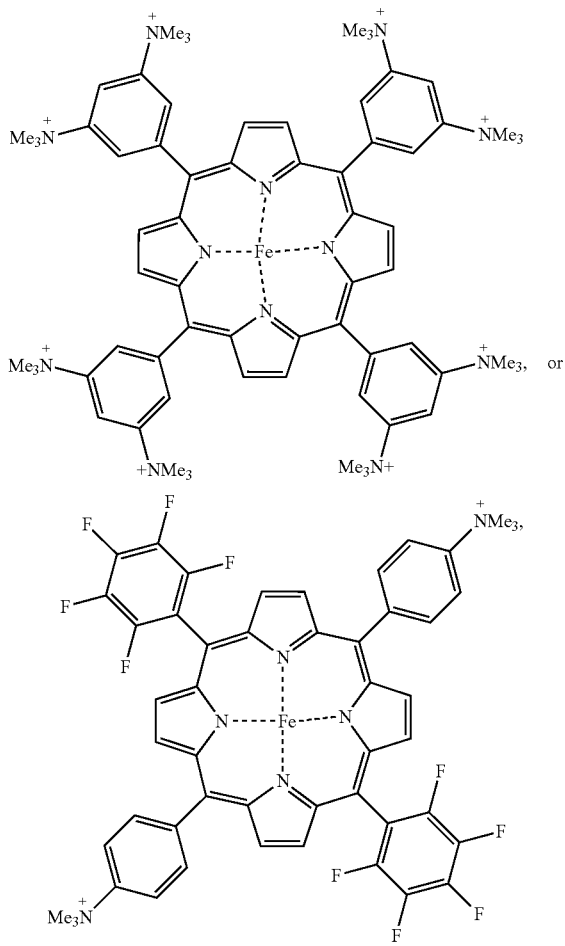

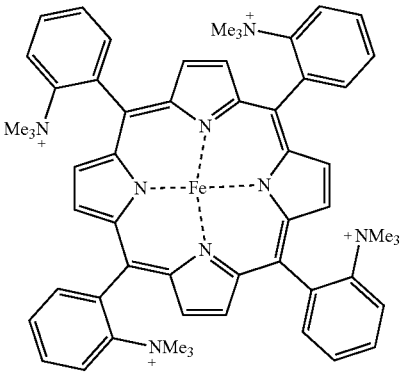

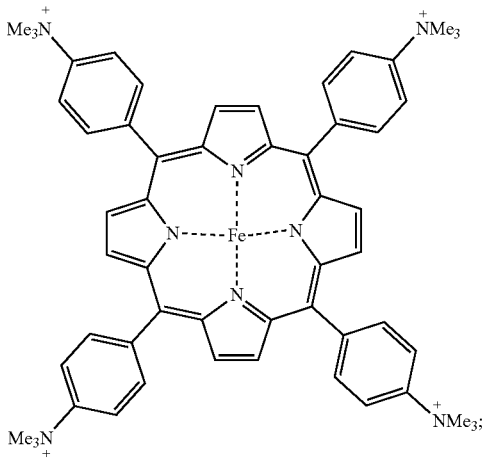

and salts thereof.

12. The photochemical composition of claim 1, wherein:

the sacrificial electron donor is the tertiary amine of formula $NR_1R_2R_3$, in which $R_1$, $R_2$ and $R_3$ are identical or different and each independently selected from a $C_1$-$C_6$ alkyl group optionally substituted with OH, $OC_1$-$C_6$ alkyl, or COOH;

the photosensitizer is the following complex:

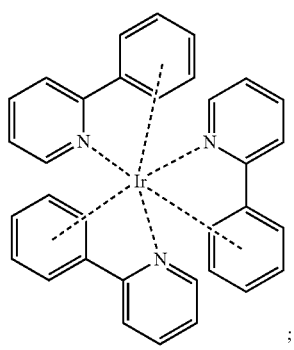

the metal porphyrin complex is the solvent is acetonitrile;

phenol or trifluoroethanol as a proton donor.

13. The photochemical composition of claim 1, wherein the concentration of the metal porphyrin complex of formula (I) as defined in claim 1 is between 1 mM and 50 mM.

14. A method for producing methane from $CO_2$ or CO, said method comprising:
  a) contacting gaseous $CO_2$ or CO, with a photochemical composition as claimed in claim 1 to obtain a solution comprising dissolved at least one of $CO_2$ and CO;
  b) irradiation of said solution with visible light; and
  c) collecting methane.

15. The method of claim 14, wherein the pressure of $CO_2$ or CO of less than 1 bar.

16. The method of claim 14, wherein the pressure of $CO_2$ or CO is of 1 bar or more.

17. The method of claim 14, wherein:
  the concentration of a sacrificial electron donor is between 10 mM and 500 mM,
  the concentration of the photosensitizer is between 50 mM and 1 mM,
  the concentration of the metal porphyrin complex of formula (I) is between 1 mM and 50 mM, the concentration of a proton donor is between 1 mM and 1 M.

18. The method of claim 14, wherein the irradiation lasts several days with wavelength λ of 400 nm or more, the reaction being stable.

* * * * *